United States Patent
Uchiyama et al.

(10) Patent No.: US 8,177,709 B2
(45) Date of Patent: May 15, 2012

(54) ROTARY SELF-PROPELLED ENDOSCOPE SYSTEM

(75) Inventors: Akio Uchiyama, Yokohama (JP);
Mitsuhiro Ito, Akiruno (JP); Seiichi Ito, Hachioji (JP); Yoshiyuki Tanii, Hamura (JP)

(73) Assignee: Olympus Medical Systems Corp., Tokyo (JP)

( * ) Notice: Subject to any disclaimer, the term of this patent is extended or adjusted under 35 U.S.C. 154(b) by 1183 days.

(21) Appl. No.: 11/906,585

(22) Filed: Oct. 3, 2007

(65) Prior Publication Data
US 2008/0086029 A1 Apr. 10, 2008

(30) Foreign Application Priority Data

Oct. 6, 2006 (JP) ................................. 2006-275496

(51) Int. Cl.
*A61B 1/00* (2006.01)
(52) U.S. Cl. ........................................ 600/114; 600/118
(58) Field of Classification Search .......... 600/114–118, 600/121, 127, 129, 137, 126, 139, 104, 106; 604/264, 271, 95.01–95.05
See application file for complete search history.

(56) References Cited

U.S. PATENT DOCUMENTS

| 4,957,482 | A * | 9/1990 | Shiber ............................. 604/22 |
| 6,726,675 | B1 * | 4/2004 | Beyar ............................ 604/510 |
| 7,199,545 | B2 * | 4/2007 | Oleynikov et al. ...... 318/568.12 |
| 7,637,864 | B2 * | 12/2009 | Yokoi et al. .................... 600/114 |
| 7,780,650 | B2 * | 8/2010 | Frassica et al. ................ 604/544 |
| 7,896,862 | B2 * | 3/2011 | Long et al. ..................... 604/528 |
| 7,959,602 | B2 * | 6/2011 | Tiedtke et al. ........... 604/100.03 |
| 2005/0119527 | A1 * | 6/2005 | Banik et al. ..................... 600/117 |
| 2005/0272976 | A1 * | 12/2005 | Tanaka et al. ................. 600/114 |
| 2009/0076383 | A1 * | 3/2009 | Toews et al. ................... 600/432 |
| 2009/0112303 | A1 * | 4/2009 | Bolduc ......................... 623/1.11 |
| 2009/0156897 | A1 * | 6/2009 | Omot et al. .................... 600/118 |
| 2009/0209812 | A1 * | 8/2009 | Omoto ........................... 600/110 |
| 2009/0281384 | A1 * | 11/2009 | Tsumaru et al. .............. 600/114 |
| 2010/0069716 | A1 * | 3/2010 | Chin et al. ..................... 600/114 |
| 2010/0185054 | A1 * | 7/2010 | Ramzipoor et al. .......... 600/114 |

FOREIGN PATENT DOCUMENTS

| JP | 10-113396 | 5/1998 |
| JP | 2006-034627 | 2/2006 |

* cited by examiner

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

A rotary self-propelled endoscope system includes an insertion section body, an insertion section, a drive unit, a torque detection unit, and a control unit. In a distal end portion of the insertion section body, a rigid distal end portion including an image pickup apparatus is disposed. The insertion section is rotatably fit to the outside of the insertion section body, and includes a rotary tubular member having a helical portion formed by a helical concave-convex portion. The drive unit applies the rotary tubular member with axial and rotational drive force. The torque detection unit detects torque information of the rotary tubular member. On the basis of the torque information detected by the torque detection unit, the control unit compares a present value with a preset limit value for controlling the torque of the rotary tubular member, and controls the drive unit on the basis of the comparison result.

6 Claims, 17 Drawing Sheets

ROTARY SELF-PROPELLED ENDOSCOPE SYSTEM

This application claims benefit of Japanese Application No. 2006-275496 filed in Japan on Oct. 6, 2006, the contents of which are incorporated by this reference.

BACKGROUND OF THE INVENTION

1. Field of the Invention

The present invention relates to a rotary self-propelled endoscope system which inserts into the body of a subject an elongated flexible tube provided with a helical portion around the outer circumference thereof.

2. Description of the Related Art

A medical endoscope enables observation of the interior of a body cavity with an elongated insertion section thereof inserted into the body cavity. Further, if necessary, the medical endoscope enables therapeutic treatment with a treatment instrument inserted into a forceps channel included in the endoscope.

The endoscope includes a bendable bending portion on the distal end side of the insertion section. The bending portion is moved and bent in the vertical or horizontal directions through the operation of a bending operation knob. The endoscope is inserted into an intricate lumen in the body cavity, such as a lumen forming a 360° loop including the large intestine, for example. In the insertion operation, a surgeon inserts the insertion section toward a site to be observed, while operating the bending operation knob to bend the bending portion and performing a twisting operation of the insertion section.

However, a high level of skill is required for the surgeon to be able to rapidly and smoothly insert the insertion section into a deep part of the intricately shaped large intestine while performing the bending operation and the twisting operation. In inserting the insertion section into the deep part of the large intestine, an inexperienced surgeon may lose the insertion direction or substantially change the lying shape of the intestine.

In light of the above, a variety of proposals have been made to improve the insertability of the insertion section. For example, Japanese Unexamined Patent Application Publication No. 10-113396 discloses a propelling device for a medical instrument capable of guiding the medical instrument into a deep part of a lumen in a body cavity with ease and with low invasion.

In the propelling device, an oblique rib with respect to the axial direction serving as a propulsive force generator is provided to a rotary member. When the rotary member is rotated in the propelling device, the rotational force of the rotary member is converted into the propulsive force by the rib. Thereby, the medical instrument connected to the propelling device is moved by the propulsive force toward the deep part.

Endoscopes using the above-described technique are divided into a variety of types. For example, endoscopes transanally inserted into the large intestine include a rotary self-propelled endoscope apparatus including an insertion section provided with a flexible and axially rotatable rotary tubular member around the outer circumference of the insertion section. According to the rotary self-propelled endoscope apparatus, the endoscope can be automatically inserted into a body cavity through the rotation of the rotary tubular member.

SUMMARY OF THE INVENTION

A rotary self-propelled endoscope system includes a flexible insertion section body, an insertion section, a drive unit, a torque detection unit, and a control unit. The insertion section body includes, in a distal end portion thereof, a rigid distal end portion including an image pickup apparatus, and is inserted into a body cavity. The insertion section is rotatably fit to the outside of the insertion section body, and includes a rotary tubular member having a helical portion formed by a helical concave-convex portion. The drive unit applies the rotary tubular member with axial and rotational drive force. The torque detection unit detects torque information of the rotary tubular member. On the basis of the torque information detected by the torque detection unit, the control unit compares a present value with a preset limit value for controlling the torque of the rotary tubular member, and controls the drive unit on the basis of the result of the comparison.

The above and other objects, features and advantages of the invention will become more clearly understood from the following description referring to the accompanying drawings.

DETAILED DESCRIPTION OF THE PREFERRED EMBODIMENTS

Embodiments of the present invention will be described below with reference to the drawings.

With reference to FIG. 1 to 13, a first embodiment of the present invention will now be described.

Figure 1:
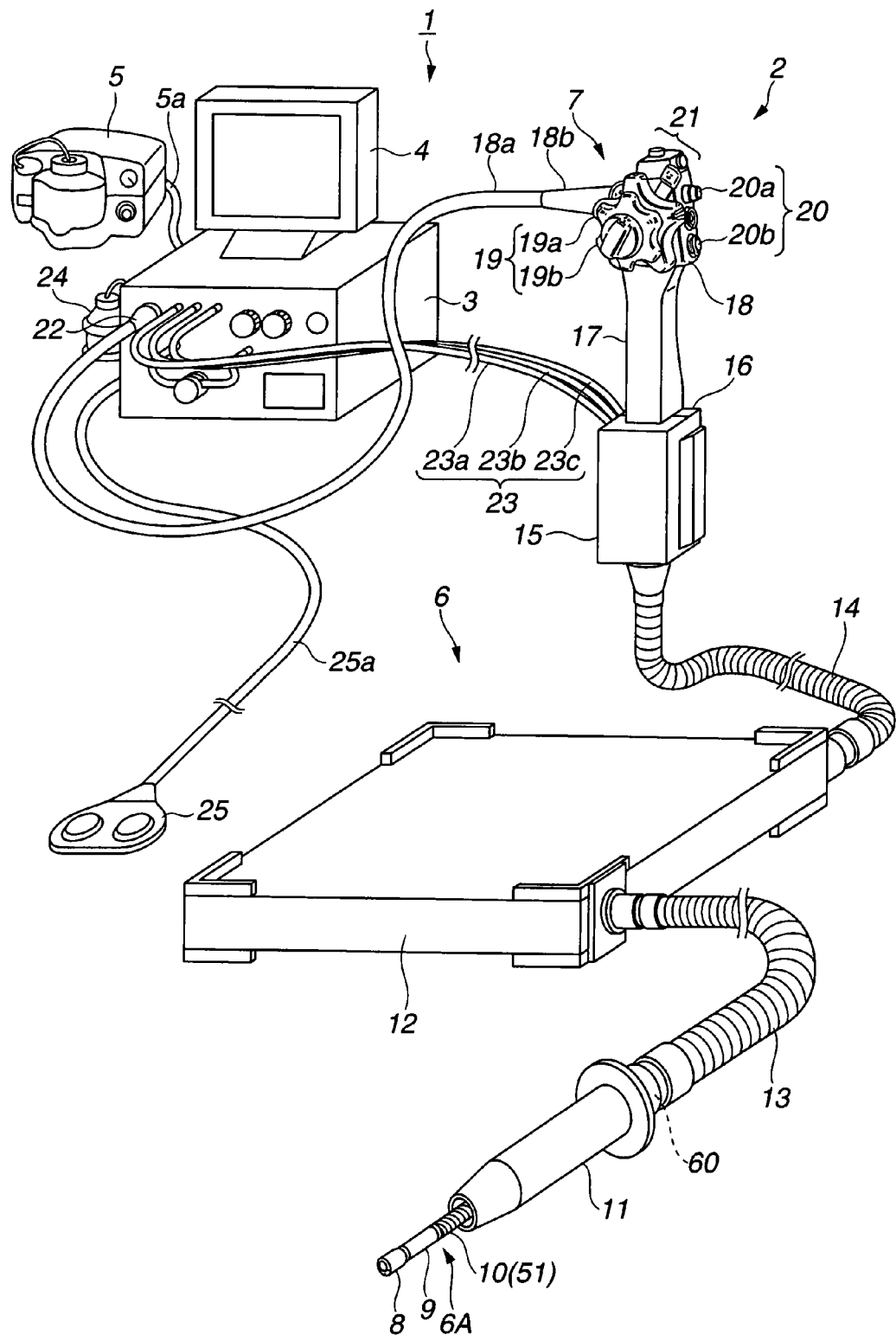
FIG. 1 is an external view illustrating an overall configuration of a rotary self-propelled endoscope system according to a first embodiment of the present invention.

As illustrated in FIG. 1, a rotary self-propelled endoscope system (hereinafter described as the endoscope system) 1 is configured to include a rotary self-propelled endoscope (hereinafter simply described as the endoscope) 2, a control device 3, a monitor 4, and a suction device 5.

The endoscope 2 includes a storage case-equipped insertion section 6 and an operation section 7. The storage case-equipped insertion section 6 is configured to include an insertion section 6A, an insertion section storage case 12, an insertion assisting device 11 serving also as a storage case, a distal end-side guide tube 13, an operation section-side guide tube 14, and a connector cover 15. The insertion section 6A is configured to include a distal end portion 8, a bending portion 9, and a rotary tubular member 51 including therein an insertion section body 10, which are disposed in this order from the distal end. The insertion assisting device 11 includes an insertion amount detection unit 60. The distal end-side guide tube 13, which is a corrugated tube, for example, is interposed between the insertion assisting device 11 and the insertion section storage case 12. The operation section-side guide tube 14, which is a corrugated tube, for example, is interposed between the operation section 7 and the insertion section storage case 12. The connector cover 15 is connected to one end of the operation section-side guide tube 14. The insertion section 6A forming the storage case-equipped insertion section 6 is attachable and detachable with respect to the operation section 7.

The operation section 7 is attachable and detachable with respect to the connector cover 15 forming the storage case-equipped insertion section 6. The operation section 7 includes a motor box 16 serving as a rotation device, a grasping portion 17, and a main operation section 18. The main operation section 18 is provided with bending operation knobs 19, fluid control buttons 20, and a variety of switches 21. The bending operation knobs 19 are used to bend the bending portion 9 of the insertion section 6A in four directions. In the present embodiment, the four directions refer to the upper, lower, left, and right directions corresponding to an endoscopic image obtained by the endoscope 2. The fluid control buttons 20 are used to instruct the ejection or suction of fluid. The variety of switches 21 are used to output instruction signals to the control device 3 to control the image pickup operation and the illumination.

The bending operation knobs 19 include two knobs 19a and 19b provided on a surface of the main operation section 18. The knobs 19a and 19b are rotatable. While the knob 19a is used to bend the bending portion 9 in the vertical directions, the knob 19b is used to bend the bending portion 9 in the horizontal directions.

From a side surface of the main operation section 18, a universal cord 18a formed by an electrical cable extends. A base portion of the universal cord 18a is provided with a bend preventing portion 18b. Meanwhile, a proximal end portion of the universal cord 18a is provided with a connector portion 22 connected to the control device 3.

A button 20a is an air or water supply button, for example. Appropriate operation of the button 20a enables gas or liquid to be ejected from a nozzle of the distal end portion 8. Meanwhile, a button 20b is a suction button, for example. The operation of the button 20b enables body wastes and so forth remaining in the body of a subject to be suctioned from distal end portion 8.

From the connector cover 15, three tubes 23 inserted through the insertion section 6A extend. The three tubes 23 include an air supply tube 23a, a water supply tube 23b, and a suction tube 23c. Proximal end portions of the tubes 23a, 23b, and 23c are connected to respective predetermined positions on the front surface of the control device 3 via attachable and detachable connectors.

The control device 3 is provided with a water supply tank 24. The water supply tank 24 stores therein sterilized water. Through a predetermined operation of the air or water supply button 20a of the main operation section 18, the sterilized water is ejected from the distal end portion 8 of the endoscope 2 through the water supply tube 23b.

Further, through another predetermined operation of the air or water supply button 20a of the main operation section 18, the air sent from a notillustrated compressor included in the control device 3 is ejected from the distal end portion 8 of the endoscope 2 through the air supply tube 23a.

Through the operation of the suction button 20b, the body wastes and so forth are suctioned from the distal end portion 8 of the endoscope 2. The aspirates are sent to the control device 3 through the suction tube 23c, and then are sent from the control device 3 to the suction device 5.

In the rotary self-propelled endoscope system 1 according to the present embodiment, the suction device 5 is used. Alternatively, a suction system installed in a hospital may be used.

The control device 3 can be connected to a foot switch 25. The foot switch 25 is a back-and-forth switch used to perform an operation of rotating the insertion section 6A of the endoscope 2 in a predetermined direction and an operation of stopping the insertion section 6A. The main operation section 18 of the operation section 7 is also provided with a back-and-forth switch (not illustrated) used to perform the operation of rotating the insertion section 6A in a predetermined direction and the operation of stopping the insertion section 6A.

The front surface of the control device 3 is provided with, for example, a power switch, a dial for changing the rotation speed of the insertion section 6A of the endoscope 2, and so forth. The motor box 16 of the operation section 7 includes therein a motor (see the reference numeral 59 of FIG. 6) for applying rotational force to the insertion section 6A. The control device 3 is electrically connected to the monitor 4. The monitor 4 displays the endoscopic image captured by the endoscope 2. A specific configuration of the control device 3 will be described later.

Figure 2:
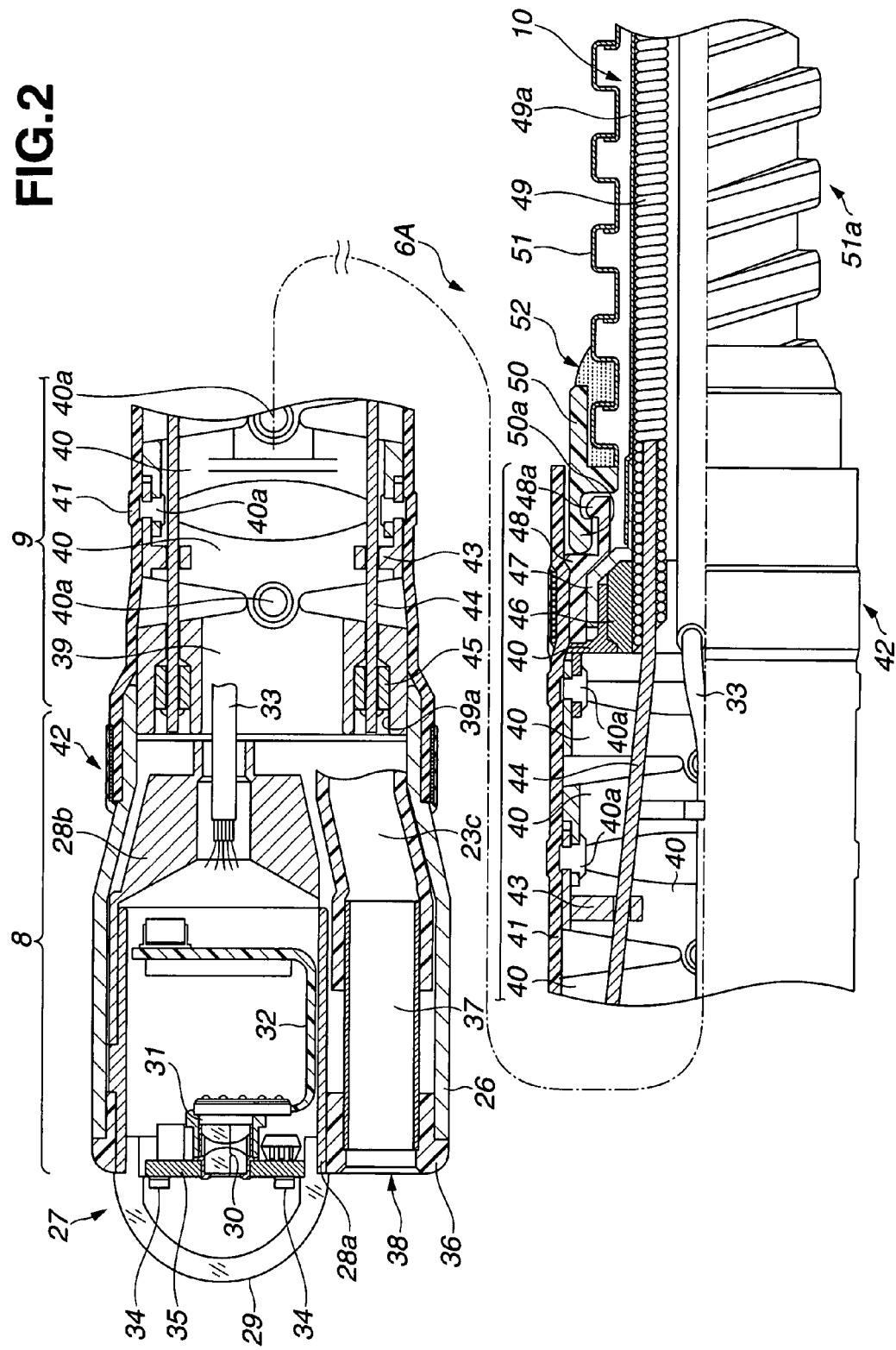
FIG. 2 is a cross-sectional view partially illustrating a distal end portion, a bending portion, and a rotary tubular member of an endoscope.
Figure 3:
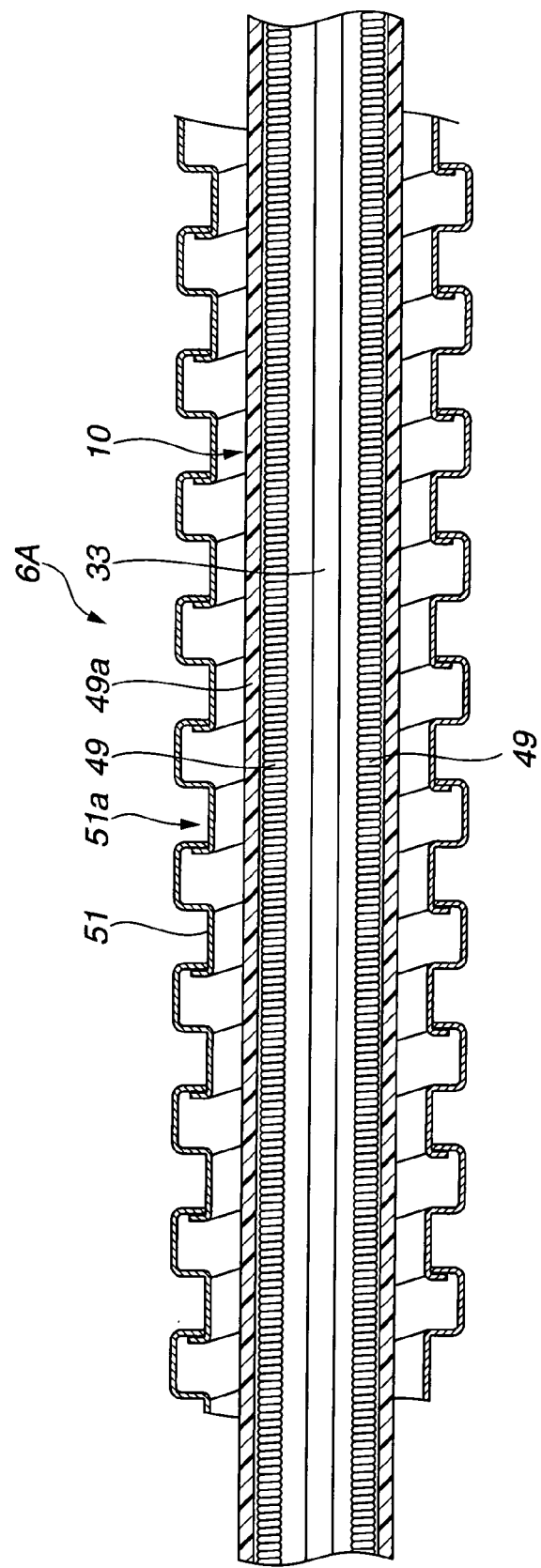
FIG. 3 a cross-sectional view illustrating the rotary tubular member and an insertion section body.

With reference to FIG. 2, description will be made of the distal end portion 8, the bending portion 9, the insertion section body 10, and the rotary tubular member 51, which form the storage case-equipped insertion section 6 of the endoscope 2.

The distal end portion 8 includes a rigid body ring 26 and an image pickup unit 27. The body ring 26 is substantially ring-shaped, and is formed of biocompatible synthetic resin.

The image pickup unit 27 forms an image pickup apparatus, the exterior of which is formed by a substantially ring-shaped retention ring 28a, a substantially ring-shaped cover ring 28b, and a dome-shaped cover member 29. The retention ring 28a is formed of synthetic resin and stored in the body ring 26. The cover ring 28b is formed of metal and fit and attached to the proximal end side of the retention ring 28a. The cover member 29 is formed of transparent and biocompatible synthetic resin and fit and attached to a distal end opening of the retention ring 28a to be air-tightly sealed thereto.

The image pickup unit 27 includes therein an object lens group 30, an image pickup device 31, such as charge coupled devices or a complementary metal oxide semiconductor, and a flexible printed circuit board (hereinafter abbreviated as the FPC) 32. The image pickup device 31 is disposed at a position at which photographing light incident upon the objective lens group 30 is condensed. The FPC 32 transmits an image signal photoelectrically converted by the image pickup device 31.

The FPC 32 is connected to a communication cable 33. The communication cable 33 is inserted through the bending portion 9 and the insertion section body 10 and connected to a not-illustrated connector provided to the connector cover 15.

A retention ring for retaining the object lens group 30 is fixed to a plate member 35. The plate member 35 is provided with a plurality of LEDs (Light-Emitting Diodes) 34, which are illuminating members surrounding the objective lens group 30. The plate member 35 is formed into a substantially circular shape, and is disposed such that the optical axis of the objective lens group 30 corresponds to the center of the plate member 35. Further, the plate member 35 is fixed to the inner surface of the cover member 29 such that the center of the cover member 29 corresponds to the center of the plate member 35.

The image pickup unit 27 is disposed at a decentered position with respect to the center of the body ring 26. The image pickup unit 27 is integrally fixed to the body ring 26 by a distal end cap 36 disposed to a distal end-side opening of the body ring 26.

The distal end cap 36 includes an opening 38, in which a distal end portion of a suction pipe 37 is disposed. The suction pipe 37 is provided to a distal end portion of the suction tube 23c. The suction pipe 37 and the suction tube 23c are disposed in a clearance formed between the body ring 26 and the retention ring 28a of the image pickup unit 27. The distal end portion of the suction pipe 37 is fixed to the opening 38 of the distal end cap 36.

Although illustration is omitted, pipe members communicating with the air supply tube 23a and the water supply tube 23b are disposed in the clearance formed between the body ring 26 and the retention ring 28a, and are fixed to the opening 38 of the distal end cap 36.

The bending portion 9 will now be described. The bending portion 9 includes a rigid distal end bending piece 39 and a plurality of rigid bending pieces 40. The respective bending pieces are rotatably coupled to one another by pivotal support members 40a. The distal end bending piece 39 is fit and attached to a proximal end opening of the body ring 26 forming the distal end portion 8. The distal end bending piece 39 and the plurality of bending pieces 40 are covered by a bending outer cover 41, which is an elastic member formed of biocompatible fluororubber, for example. A distal end portion of the bending outer cover 41 is fixed to a proximal end portion of the body ring 26 by a bobbin adhesive portion 42.

The plurality of bending pieces 40 include wire guides 43 projecting from the inner circumferential surface thereof toward the center thereof. Bending operation wires 44 are inserted through the wire guides 43.

Four bending operation wires 44 are disposed in the bending portion 9. FIG. 2 shows only two of the bending operation wires 44. The distal end bending piece 39 is formed with four lock holes 39a, in each of which a cylindrical lock member 45, for example, is fixed. The distal end of each of the bending operation wires 44 is joined to the corresponding lock member 45 with a solder or the like.

The four lock holes 39a are formed in a surface of the distal end bending piece 39 perpendicular to the axis of the distal end bending piece 39 at intervals of approximately 90 degrees. The four lock holes 39a correspond to the upper, lower, left, and right sides of the surface of the distal end bending piece 39.

The bending operation wires 44 are inserted through the insertion section body 10, and extend to the connector cover 15. A proximal end portion of each of the bending operation wires 44 is provided with a not-illustrated wire retainer. In a state in which the connector cover 15 is integrated with the motor box 16, the wire retainers of the bending operation wires 44 are respectively connected to not-illustrated connecting members provided in the grasping portion 17.

Each of the connecting members is connected to a not-illustrated chain included in a not-illustrated bending operation mechanism which operates in conjunction with the bending operation knobs 19 provided to the main operation section 18. That is, when the bending operation knobs 19 are operated and rotated, the respective connecting members are pulled or loosened by the bending operation mechanism. Then, in conjunction with the movement, the respective bending operation wires 44 are pulled or loosened.

When the four bending operation wires 44 are respectively pulled and loosened, therefore, the plurality of bending pieces 40 correspondingly rotate, and the bending portion 9 is bent in the above-described four directions.

Inside the bending piece 40 located on the most proximal end of the bending portion 9, a first ferrule 46 formed of metal is fit and attached to the inside of the bending piece 40 to fix coil pipes to the bending piece 40. Further, a second ferrule 47 formed of metal is fit and attached to the outer circumference of the bending piece 40 on the most proximal end to fix an inner layer tube to the bending piece 40. Furthermore, a third ferrule 48 formed of synthetic resin is fit and attached to the outer circumference of the second ferrule 47 to rotatably engage the rotary tubular member 51. The ferrules 46, 47, and 48 are firmly fixed by an adhesive agent or the like. A proximal end portion of the above-described bending outer cover 41 is fixed to the third ferrule 48 by the bobbin adhesive portion 42. To the inner circumferential surface of the first ferrule 46, a distal end portion of each of four coil sheathes 49 is fixed by brazing or the like. The above-described bending operation wires 44 are inserted through the respective coil sheathes 49 and extend to the proximal end side. Each of the coil sheathes 49 has an incompressible structure formed by a wire closely wound into a pipe shape.

A proximal end portion of the second ferrule 47 is fixed with a distal end portion of a flexible inner layer tube 49a inserted through the insertion section body 10. The inner layer tube 49a may be a flexible mesh tube formed by thin wires woven into a tubular shape.

A proximal end portion of the third ferrule 48 having a reduced diameter is provided with a flange 48a. The third ferrule 48 is completely covered by the bending outer cover 41, and a clearance is formed between the bending outer cover 41 and the outer circumference of the flange 48a. In the present embodiment, the endoscope 2 includes the bending portion 9. Needless to say, however, the present invention is also applicable to an endoscope not including the bending portion 9.

Description will now be made of the insertion section body 10 and the rotary tubular member 51, which form the insertion section 6A. The insertion section 6A includes the insertion section body 10 and the rotary tubular member 51. The insertion section body 10 is formed by the inner layer tube 49a, the four coil sheathes 49, through which the respective bending operation wires 44 are inserted, the communication cable 33, and the respective tubes 23 not illustrated. The inner layer tube 49a is a tube for protecting the components included therein. In the inner layer tube 49a, the coil sheathes 49, the communication cable 33, and the tubes 23 are inserted.

A distal end portion of the rotary tubular member 51 includes a ferrule 50 for connection purpose. The ferrule 50 is formed of synthetic resin and fixed to the distal end portion of the rotary tubular member 51 by an adhesive agent 52. A distal end portion of the ferrule 50 is formed with a concave-convex portion 50a. The concave-convex portion 50a engages with the above-described flange 48a of the third ferrule 48 of the bending portion 9, and has a snap-fit function. The ferrule 50 is axially rotatable with respect to the third ferrule 48.

The rotary tubular member 51 is a flexible tubular member formed by a helically wound biocompatible metal plate member processed to have a cross section formed with a convex portion and a concave portion. The rotary tubular member 51 forms a helical portion 51a formed with a helical convex portion around the outer circumferential surface thereof, with the concave portion and the convex portion engaging with each other substantially with no gap therebetween.

Specifically, the rotary tubular member 51 is a helical tube designed in consideration of the insertability into the body cavity. Further, the rotary tubular member 51 is formed of stainless steel, for example, and set to a predetermined diameter size. In the rotary tubular member 51, such factors as the pitch and the angle of the helix can be variously set by appropriately setting the sizes of the concave portion and the convex portion formed on the plate member.

The rotary tubular member 51 is configured to be rotatable about the axis of the insertion direction. Therefore, when the rotary tubular member 51 rotates, the helical portion 51a formed on the outer circumferential surface of the rotary tubular member 51 comes in contact with the inner wall of the body cavity of the subject, and thrust force is generated. Thereby, the rotary tubular member 51 propels itself in the insertion direction.

As the rotary tubular member 51 advances, the ferrule 50 fixed to the distal end portion of the rotary tubular member 51 comes in contact with the third ferrule 48, which is provided to the proximal end portion of the bending portion 9, and presses the bending portion 9. Thereby, the entirety of the insertion section 6A including the distal end portion 8 is applied with propulsive force which advances the insertion section 6A toward a deep part of the body cavity.

The rotary tubular member 51 is applied with rotational drive force by the motor 59 disposed in the motor box 16 of the operation section 7.

The present embodiment is configured to transmit the rotational drive force of the motor 59 to the proximal end side of the rotary tubular member 51 to rotate the rotary tubular member 51. However, the configuration for rotating the rotary tubular member 51 is not limited to the above. For example, therefore, the configuration may be such that the rotational drive force of the motor 59 is transmitted to an intermediate portion or the distal end portion of the rotary tubular member 51.

The rotary tubular member 51 is disposed around the outer circumference of the inner layer tube 49a forming the insertion section body 10, and is rotatable about the long axis of the insertion section body 10.

Figure 4:
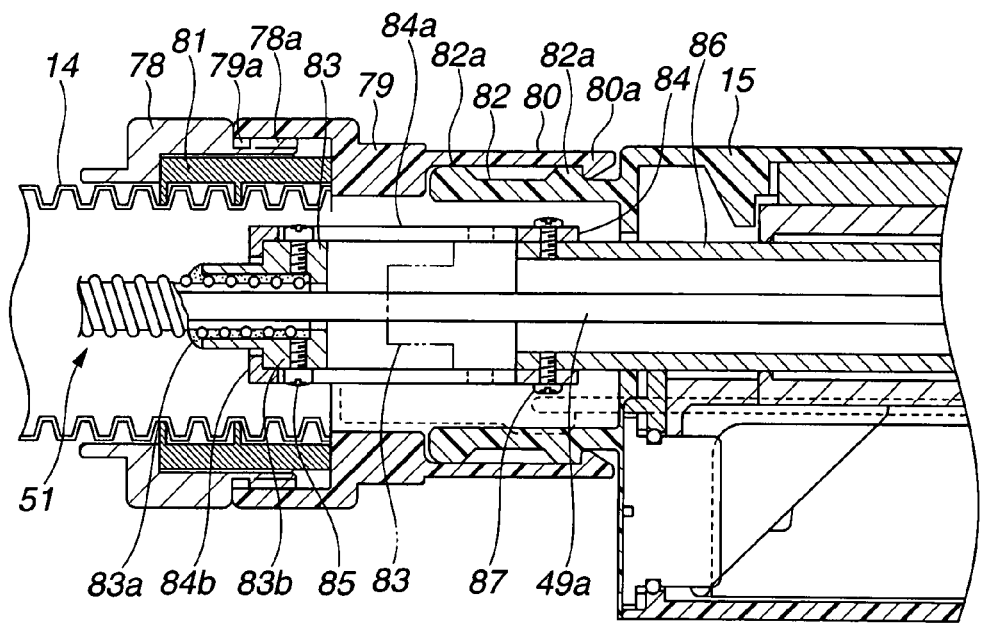
FIG. 4 is a cross-sectional view partially illustrating a connector cover connected to an operation section-side guide tube.

With reference to FIG. 4, the proximal end side of the storage case-equipped insertion section 6 will now be described. Description will be first made of the connection between the operation section-side guide tube 14 and the connector cover 15. As illustrated in FIG. 4, a proximal end portion of the operation section-side guide tube 14 is provided with a fifth fixing ring 78 and a fastening ring 81. The fifth fixing ring 78 has a substantially cylindrical shape, and is formed of a rigid material, such as metal or synthetic resin. The fastening ring 81 is retained in the inner hole of the fifth fixing ring 78, with a connecting tubular member 79 screwed to the fifth fixing ring 78. The connecting tubular member 79 is formed of synthetic resin.

The fifth fixing ring 78 includes a diameter-expanded portion in a middle portion thereof, and is formed with a male screw 78a on the outer circumference of a diameter-reduced portion on the proximal end side thereof. Meanwhile, the connecting tubular member 79 includes a diameter-expanded portion in a distal end portion thereof, and is formed with a female screw 79a on the inner circumferential surface of the diameter-expanded portion. The female screw 79a is screwed to the male screw 78a. A proximal end portion of the connecting tubular member 79 is provided with a lock portion 80 which is attachable and detachable with respect to the connector cover 15.

With the male screw 78a and the female screw 79a screwed to each other, the fifth fixing ring 78 and the connecting tubular member 79 are connected to each other, and the fastening ring 81 is disposed inside the fifth fixing ring 78 in the connected state. In the connected state, the proximal end portion of the operation section-side guide tube 14 is compressed, and the proximal end of the operation section-side guide tube 14 is in contact with and pressed by an end surface of the connecting tubular member 79. In the connected state, therefore, the watertightness is maintained between the fifth fixing ring 78 of the operation section-side guide tube 14 and the connecting tubular member 79.

The lock portion 80 of the connecting tubular member 79 connected to the connector cover 15 is connected to the connector cover 15. Specifically, the connector cover 15 includes a connecting portion 82, which is formed with outward flanges 82a in a distal end portion and a proximal end portion thereof. The lock portion 80 of the connecting tubular member 79 is fit to the outside of the connecting portion 82 to be connected to the connecting portion 82.

A proximal end portion of the lock portion 80 is formed with a projection 80a projecting toward the inner circumference of the connecting tubular member 79. Thus, with the projection 80a locked by the outward flange 82a formed on the proximal end portion of the connecting portion 82, the lock portion 80 of the connecting tubular member 79 is connected to the connecting portion 82 of the connector cover 15.

With the projection 80a of the lock portion 80 locked by the outward flange 82a of the connector cover 15, the connecting tubular member 79 is axially rotatable with respect to the connector cover 15. Therefore, the operation section-side guide tube 14 connected to the connecting tubular member 79 is also rotatable with respect to the connector cover 15.

In the connecting portion of the operation section-side guide tube 14 and the connector cover 15, a proximal end portion of the helical portion 51a is fixed to a proximal end-side ferrule 83 by an adhesive agent 83a. The proximal end-side ferrule 83 is slidably fit and inserted into a slide tube 84. The slide tube 84 is formed with two long holes 84a which are symmetrically disposed in the vertical direction in the figure, and in which head portions of male screws 85 are disposed.

The proximal end-side ferrule 83 is formed with female screws 83b, into which the male screws 85 disposed in the long holes 84a of the slide tube 84 are screwed. A proximal end portion of the slide tube 84 is integrally connected to a distal end portion of a rotary shaft 86 by fixing screws 87. Although not illustrated, the rotary shaft 86 is supported so as to rotate inside the connector cover 15.

The distal end side of the slide tube 84 is formed with an inward flange 84b to prevent the proximal end-side ferrule 83 from dropping from the slide tube 84. The proximal end-side ferrule 83 is movable in the longitudinal direction between the inward flange 84b and the distal end surface of the rotary shaft 86. Therefore, even if the rotary tubular member 51 is applied with torque in the rotational movement thereof, the proximal end-side ferrule 83 performs a sliding movement. Accordingly, the rotary tubular member 51 expands and contracts in the longitudinal direction, and is prevented from becoming inflexible. Accordingly, deterioration of the insertability can be prevented.

Figure 5:
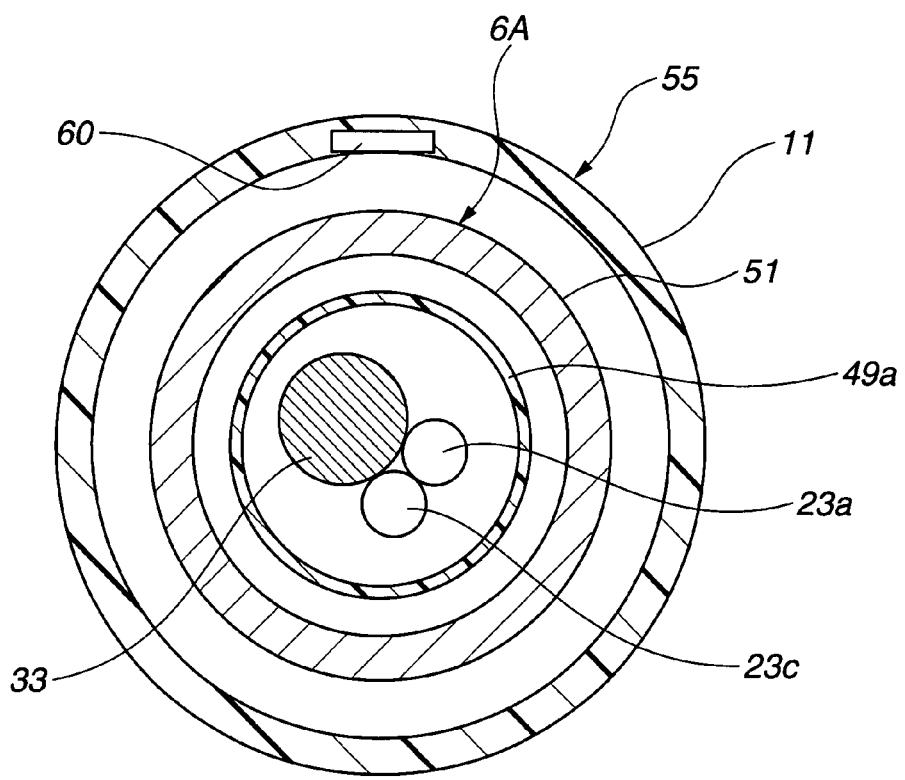
FIG. 5 is a cross-sectional view illustrating an insertion assisting device provided with an insertion amount detection unit.
Figure 8:
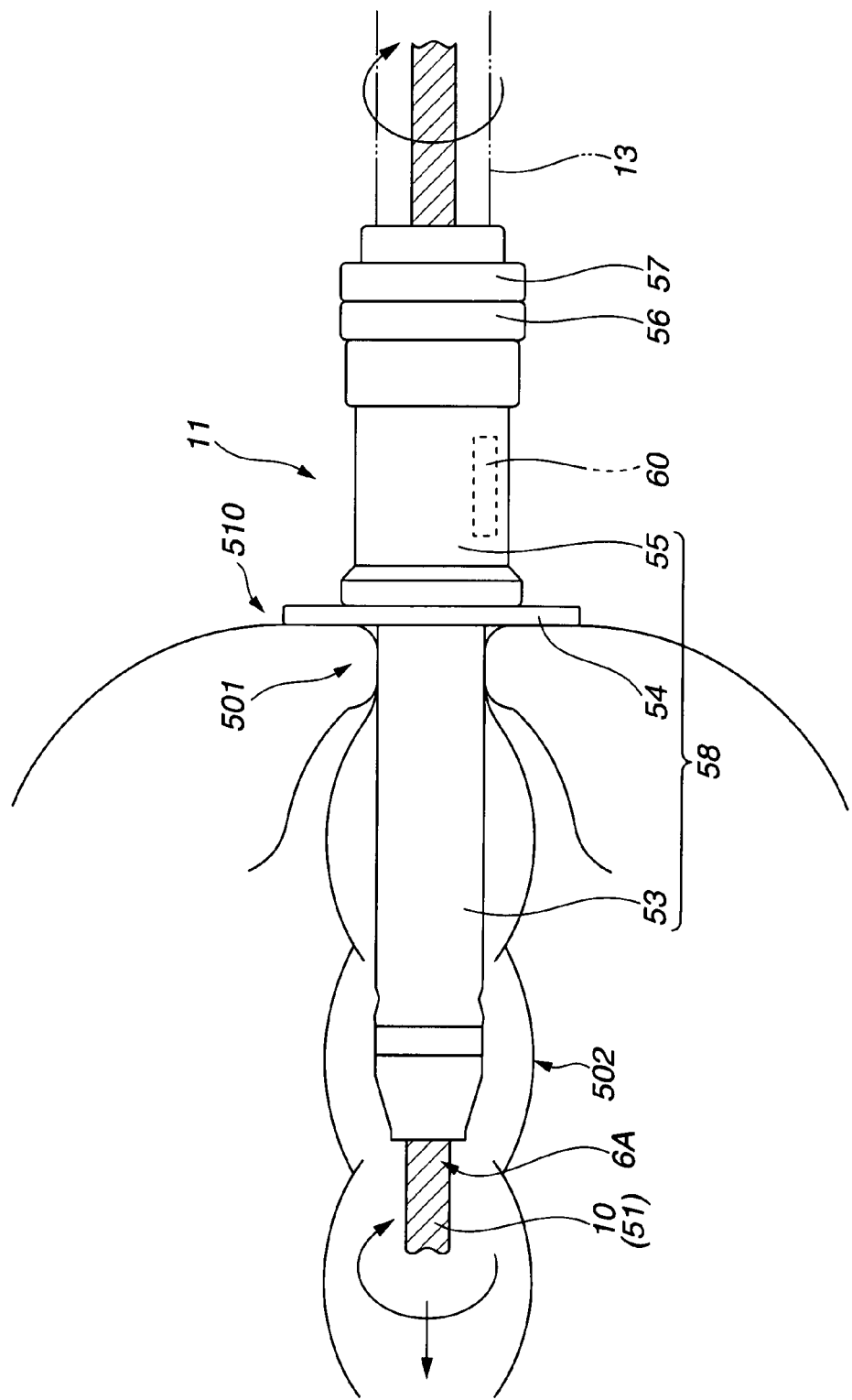
FIG. 8 is an explanatory diagram illustrating a state in which an insertion assisting device is inserted from the anus of a patient into the rectum.

With reference to FIGS. 5 and 8, the insertion assisting device 11 will now be described. As illustrated in FIG. 8, the insertion assisting device 11, through which the insertion section 6A is inserted, is configured to include an assisting device insertion section 58, and two connecting rings 56 and 57 connected to the distal end-side guide tube 13. The assisting device insertion section 58 includes a tubular insertion pipe 53, a doughnut disk-shaped abutting portion 54 forming an outward flange, and a retention pipe 55.

The insertion assisting device 11 is provided with the insertion amount detection unit 60 for detecting the insertion amount of the insertion section 6A. The insertion amount detection unit 60 is provided to, for example, the inner circumferential surface of the retention pipe 55 of the insertion assisting device 11, as illustrated in FIGS. 5 and 8, for example.

The insertion amount detection unit 60 is configured to include an optical sensor detection unit formed by, for example, a light-emitting element and a light-receiving element. The insertion amount detection unit 60 is electrically connected to the control device 3 via a not-illustrated signal line.

When the helical portion 51a rotates, the optical sensor detection unit optically detects the convex or concave portion of the rotating helical portion 51a on the basis of the light emitted by the optical sensor detection unit. Thereby, the insertion amount detection unit 60 detects the insertion amount of the insertion section body 10.

The insertion amount detection unit 60 is not limited to the one using the optical sensor detection unit. Thus, the insertion amount detection unit 60 may be configured to detect the insertion amount of the rotary tubular member 51 with the use of a linear potentiometer or the like, for example.

In the present embodiment, description has been made of the configuration in which the insertion amount detection unit 60 is provided inside the insertion assisting device 11. However, the configuration is not limited to the above. For example, the configuration may be modified such that the insertion amount detection unit 60 is provided inside the motor box 16 to detect the insertion amount of the insertion section 6A and output the result of the detection to a rotation control unit 66 provided in the control device 3.

Figure 6:
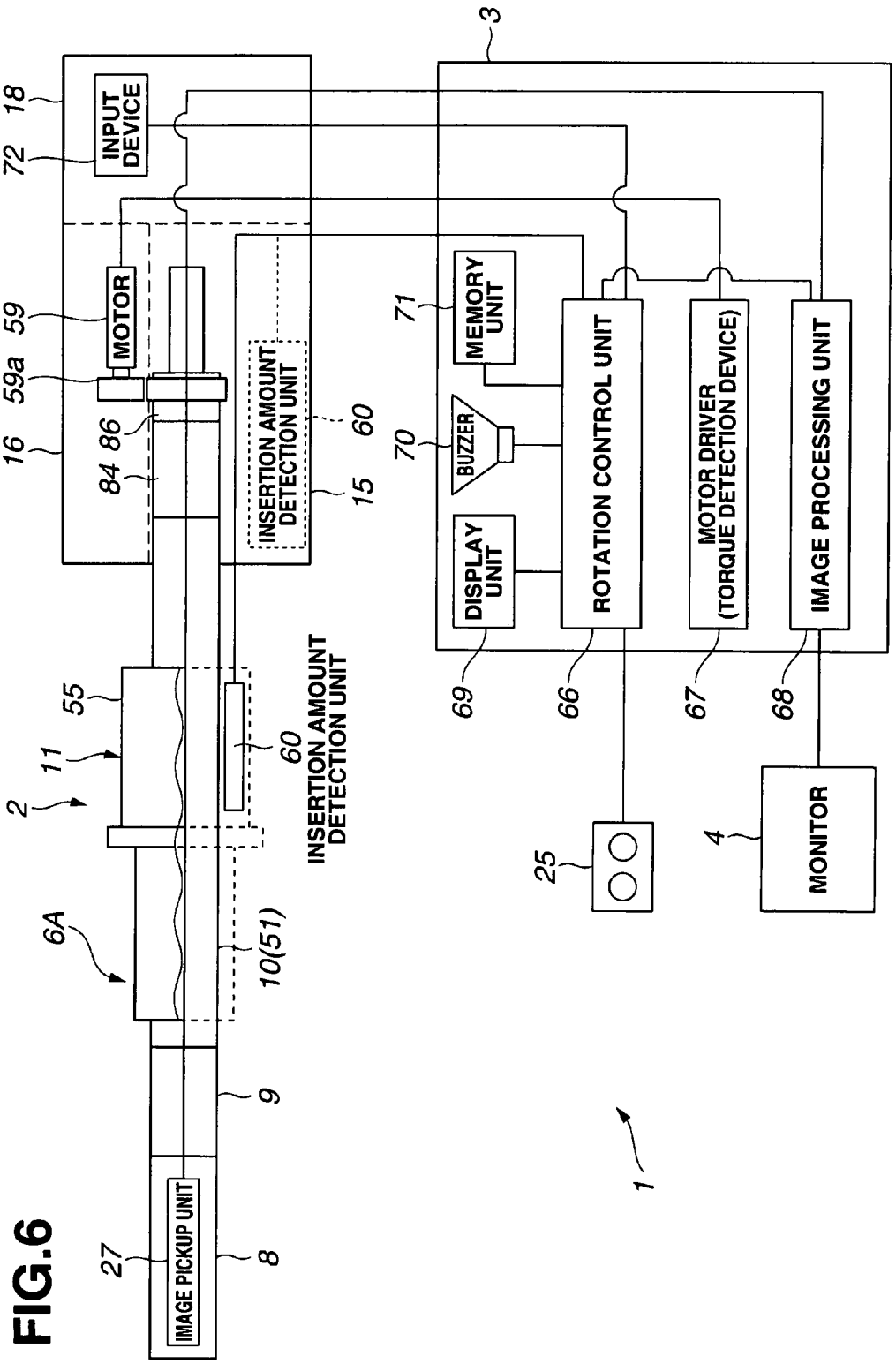
FIG. 6 is a block diagram illustrating an overall electrical configuration of the rotary self-propelled endoscope system.

With reference to FIG. 6, description will now be made of an electrical configuration of essential parts included in the endoscope 2 and the control device 3 of the rotary self-propelled endoscope system 1 according to the present embodiment. As described above, the endoscope 2 and the control device 3 are electrically connected to each other by the universal cord 18a. The endoscope 2 according to the present embodiment includes the image pickup unit 27 in the distal end portion 8. Further, the motor box 16 of the endoscope 2 includes therein the motor 59 for rotating the rotary tubular member 51, which is inserted over the insertion section body 10.

The main operation section 18 of the operation section 7 includes therein an input device 72 for rotating and stopping the motor 59, and the insertion amount detection unit 60. The above respective devices included in the endoscope 2 are electrically connected to the respective parts included in the control device 3.

Specifically, the control device 3 includes the rotation control unit 66, a motor driver 67, an image processing unit 68, a display unit 69, a buzzer 70, and a memory unit 71. The motor driver 67 is a torque detection device. The image processing unit 68 outputs an image signal to the monitor 4. The display unit 69 is an alarm lamp capable of displaying a variety of operation states and so forth on a liquid crystal monitor, for example. The buzzer 70 is an alarm unit. The memory unit 71 is storage means for storing, for example, a preset torque value in accordance with the insertion amount of the insertion section 6A.

The image pickup unit 27 is electrically connected to the image processing unit 68, which is electrically connected to the rotation control unit 66. The image processing unit 68 receives an image signal inputted from the image pickup unit 27 and outputs the image signal to the monitor 4. Via the image processing unit 68, electric power is supplied to the respective LEDs 34 of the image pickup unit 27.

The motor 59 included in the motor box 16 is electrically connected to the motor driver 67, which is electrically connected to the rotation control unit 66. The motor driver 67 detects the rotational torque of the motor 59 and outputs a detection signal to the rotation control unit 66. On the basis of the detection signal outputted from the motor driver 67, the rotation control unit 66 controls the driving operation of the motor driver 67. The motor driver 67 forms the torque detection device, and the rotational torque of the motor 59 corresponds to torque information. The rotation control unit 66 forms a control unit.

The insertion amount detection unit 60 is electrically connected to the rotation control unit 66 included in the control device 3. The detection signal for informing the insertion amount of the insertion section 6A detected by the optical sensor detection unit is outputted to the rotation control unit 66.

The input device 72 of the main operation section 18 and the foot switch 25 described with reference to FIG. 1 are electrically connected to the rotation control unit 66. The input device 72 and the foot switch 25 are operated to switch between ON and OFF of the motor 59 which rotates the rotary tubular member 51. The motor 59 can be turned ON and OFF through the operation of either one of the input device 72 and the foot switch 25.

The rotation control unit 66 is electrically connected to the display unit 69 and the buzzer 70 to control the display unit 69 and the buzzer 70.

The endoscope 2 is configured such that, when the connector cover 15 is connected to the motor box 16, a gear 86a provided to the rotary shaft 86 meshes with a gear 59a of the motor 59 provided in the motor box 16. Accordingly, the drive force of the motor 59 is transmitted to the rotary shaft 86 via the gears 59a and 86a, and the helical portion 51a is rotated about the longitudinal axis thereof via the proximal end-side ferrule 83.

That is, the rotational drive force sent from the motor box 16 is transmitted to the proximal end portion of the helical portion 51a. The inner layer tube 49a inserted through the helical portion 51a is configured to extend from inside the connector cover 15 to the helical portion 51a through the rotary shaft 86.

Each of the connector cover 15 and the motor box 16 includes a not-illustrated electrical connector. In a state in which the connector cover 15 and the motor box 16 are connected to each other, the electrical connectors are electrically connected so as to electrically connect the image pickup unit 27 to the control device 3.

In the present embodiment, the memory unit 71 of the control device 3 stores a preset torque data value in accordance with the insertion amount of the insertion section 6A. The memory unit 71 is controlled by the rotation control unit 66 in the operation of reading the stored torque data value or writing a torque data value.

In the present embodiment, the torque data value is stored in the memory unit 71. In place of the torque value, the value of current flowing through the motor 59 in accordance with the insertion amount of the insertion section 6A may be previously stored. The torque data value stored in the memory unit 71 corresponds to a limit value.

The rotation control unit 66 changes and sets the preset limit value in accordance with the insertion amount of the insertion section 6A into the body cavity detected by the insertion amount detection unit 60. Then, the rotation control unit 66 compares the thus set limit value with the torque data value detected by the motor driver 67, which serves as the torque detection unit, and controls the motor driver 67 on the basis of the result of the comparison.

Specifically, the rotation control unit 66 reads from the memory unit 71 the torque data value in accordance with the insertion amount, i.e., the result of the detection obtained from the insertion amount detection unit 60. Further, the rotation control unit 66 sets the thus read torque data value as a torque limit value 100, which is the limit value used in the drive control of the motor driver 67.

Figure 13:
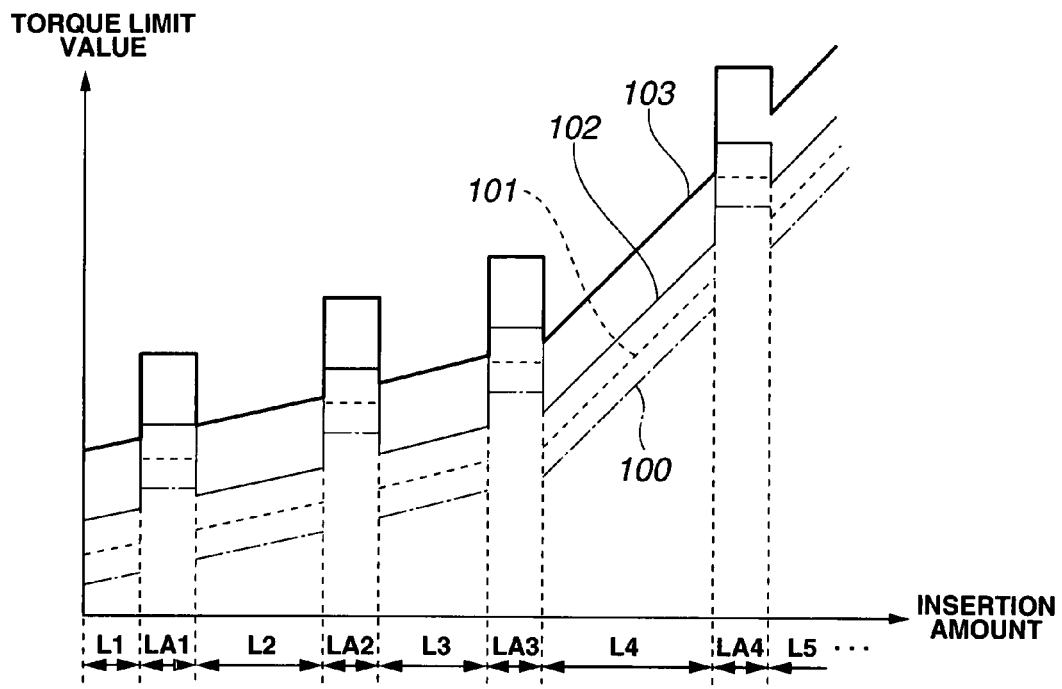
FIG. 13 is a graph showing torque limit values in accordance with insertion amounts, which are used in determination control performed by the rotation control unit.

In setting the torque limit value, such factors as individual variation among patients are taken into account. That is, the rotation control unit 66 can, for example, set the torque limit value in a plurality of patterns of different dimensions in accordance with the state inside the body cavity of the patient. As shown in FIG. 13, using the set torque limit value 100 as the reference value, the rotation control unit 66 may set torque limit values equal to or larger than the value in accordance with a plurality of control phases, such as the first torque limit value 100 to the fourth torque limit value 103, for example.

The torque limit values shown in FIG. 13 are set by the rotation control unit 66 in accordance with the insertion amounts of the insertion section 6A. That is, in the present embodiment, the first torque limit value 100 serving as the reference value and indicated by the alternate long and short dash line in FIG. 13 is set through the control by the rotation control unit 66.

If the torque limit values in accordance with the plurality of control phases are unnecessary, only the first torque limit value 100 serving as the reference value may be set. Further, to switch between the setting of only the first torque limit value 100 and the setting of the first torque limit value 100 to the fourth torque limit value 103, for example, in accordance with the plurality of control phases, a mode selecting operation is performed through the input device 72 to switch the setting.

To activate a mode for switching the torque limit value in accordance with the plurality of control phases from the first torque limit value 100 to the fourth torque limit value 103, for example, the respective torque limit values 100, 101, 102, and 103 are set, as shown in FIG. 13. That is, as indicated by the broken line in the figure, the second torque limit value 101 is larger than the first torque limit value 100. Further, as indicated by the thin solid line in the figure, the third torque limit value 102 is larger than the second torque limit value 101. Furthermore, as indicated by the thick solid line in the figure, the fourth torque limit value 103 is larger than the third torque limit value 102. The torque limit values are not limited to the above torque limit values 100, 101, 102, and 103. Thus, a further plurality of torque limit values may be set in addition to the above torque limit values.

Figure 9:
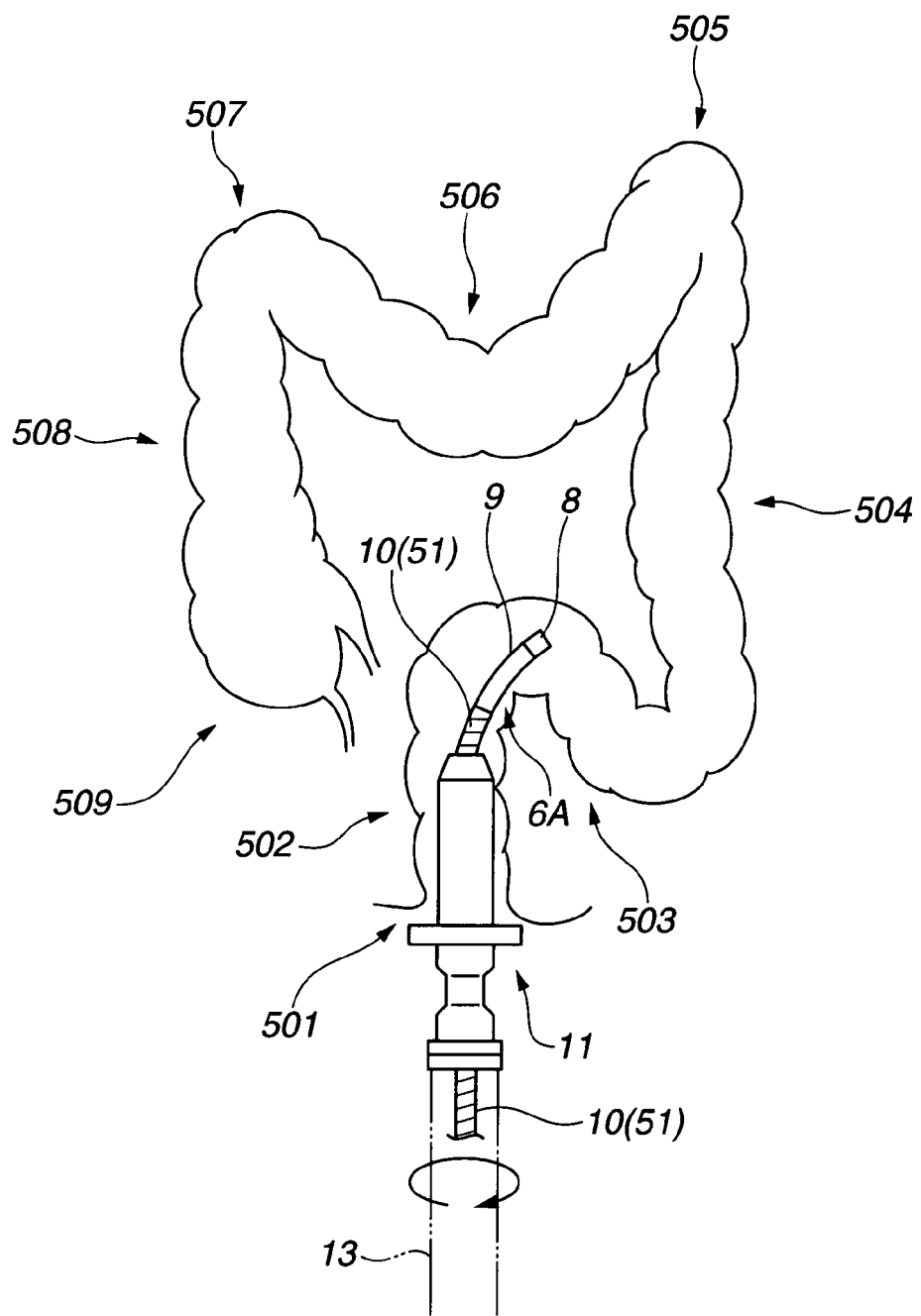
FIG. 9 is an explanatory diagram illustrating a state in which the insertion section body inserted into the large intestine via the insertion assisting device has reached the sigmoid colon.

Insertion amounts L1, L2, L3, L4, and L5 shown in FIG. 13 respectively represent the range from the anus 501 to the rectum 502, the range of the sigmoid colon 503, the range of the descending colon 504, the range of the transverse colon 506, and the range from the ascending colon 508 to the cecum 509, which are illustrated in FIG. 9. The respective ranges of the insertion amounts L1, L2, L3, L4, and L5 include therebetween insertion amounts LA1, LA2, LA3, and LA4. The insertion amounts LA1, LA2, LA3, and LA4 respectively represent the range of a winding portion of the sigmoid colon 503, the range of a winding portion between the sigmoid colon 503 and the descending colon 504 of low mobility, the range of a splenic flexure 505 between the descending colon 504 and the transverse colon 506 of high mobility, and the range of a hepatic flexure 507 between the transverse colon 506 and the ascending colon 508.

The ranges of the insertion amounts L1 to L5 and so forth shown in FIG. 13 are examples, similarly to the above-described torque limit values. Therefore, the ranges of the insertion amounts are not limited to the above, and thus may be arbitrarily changed and set.

A use example of the rotary self-propelled endoscope system 1 will now be described. In the following description, colonoscopy will be taken as an example with reference to FIG. 7 to 10. It is now assumed that the colonoscopy, for example, is performed with the use of the endoscope system 1. In the procedure, a surgeon inserts the insertion assisting device 11 into the anus of a patient lying on a bed, for example. The insertion section 6A is stored in the insertion section storage case 12, bent in such a curve as illustrated in FIG. 7.

In the insertion assisting device 11, the abutting portion 54 abuts on the buttocks 510 in the vicinity of the anus 501 of the patient, as illustrated in FIG. 8. Thereby, only the insertion pipe 53 is inserted into the rectum 502. In other words, the abutting portion 54 prevents the insertion assisting device 11 from being entirely inserted into the rectum 502. The surgeon fixes the abutting portion 54 to the buttocks 510 of the patient with a tape or the like.

Then, the surgeon grasps the grasping portion 17 of the operation section 7, and rotates the helical portion 51a of the insertion section body 10 about the longitudinal axis of the helical portion 51a through the foot operation of the foot switch 25 or the hand operation of the back-and-forth switch provided to the main operation section 18.

Figure 7:
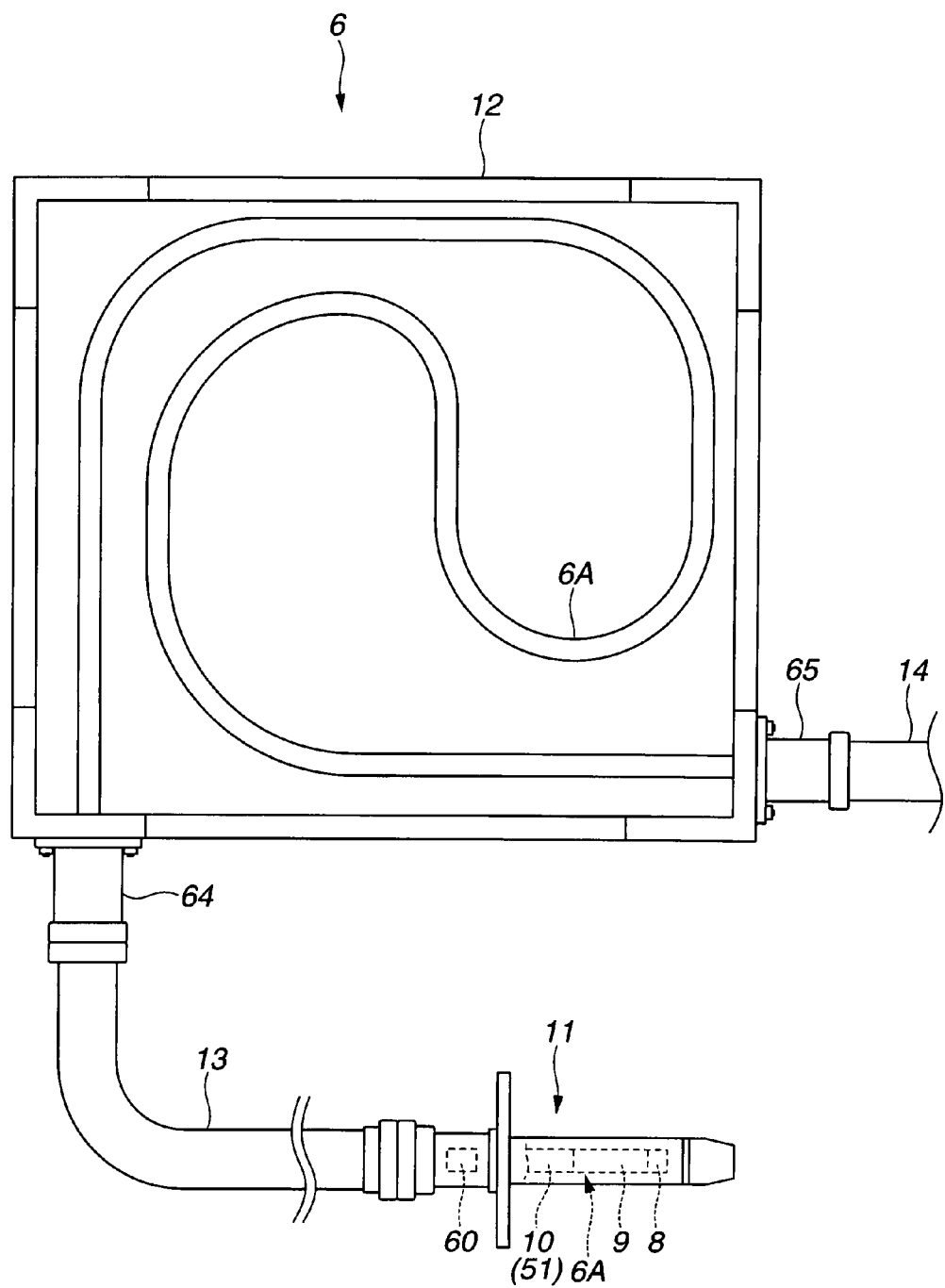
FIG. 7 is a diagram for explaining a storage case-equipped insertion section, which includes a top view of a storage case of the storage case-equipped insertion section.

As illustrated in FIG. 7, the insertion section storage case 12 is provided with guide tube fixing members 64 and 65 connected to one end portions of the guide tubes 13 and 14, respectively. Inside the guide tube fixing member 64 connected to the distal end-side guide tube 13, a not-illustrated rubber plate or the like is provided which is fit to the helical portion 51a to apply the helical portion 51a with propulsive force by using the rotational force applied to the helical portion 51a.

When the surgeon drives and rotates the motor 59, the rotational force is transmitted to the helical portion 51a. Then, the entirety of the helical portion 51a is axially rotated in a predetermined direction, as indicated by the arrow in FIG. 8, and is applied with the propulsive force by the guide tube fixing member 64 of the insertion section storage case 12.

In the helical portion 51a applied with the propulsive force, the distal end-side ferrule 50 presses the third ferrule 48, which is connected to the helical tube. Thereby, the entirety of the insertion section body 10 including the distal end portion 8 and the bending portion 9, i.e., the insertion section 6A is advanced by the propulsive force of the helical portion 51a toward the inside of the large intestine through the distal end-side guide tube 13 and the insertion assisting device 1.

That is, while lightly grasping the retention pipe 55 of the insertion assisting device 11, the surgeon can cause the insertion section 6A to advance solely with the propulsive force applied to the insertion section 6A in the guide tube fixing member 64, without grasping and pushing forward the insertion section 6A.

When the insertion section 6A is pushed out of the insertion assisting device 11 into the large intestine, the helical portion 51a comes in contact with the folds of the intestinal wall. The contact state of the helical portion 51a and the intestinal wall corresponds to the relationship between a male screw and a female screw. Therefore, the rotating helical portion 51a is smoothly advanced by the propulsive force applied thereto in the guide tube fixing member 64 and the propulsive force generated from the contact of the helical portion 51a and the folds of the intestinal wall. As a result, the insertion section 6A is advanced from the rectum 502 toward the sigmoid colon 503.

Then, as illustrated in FIG. 9, the distal end portion 8 and the bending portion 9 of the insertion section 6A reach the sigmoid colon 503. In the process, while watching the endoscopic image displayed on the monitor 4, the surgeon operates the bending operation knobs 19 of the main operation section 18 to perform, for example, an operation of bending the bending portion 9 to be adjusted to the winding shape of the sigmoid colon 503.

Through the operation by the surgeon for bending the bending portion 9, the distal end portion 8 of the insertion section 6A applied with the propulsive force advances and passes through the sigmoid colon 503, in which the insertion operation is difficult to perform. As the insertion section 6A is inserted into a deep part of the large intestine, the length of the contact area between the helical portion 51a and the intestinal wall is increased.

Therefore, the insertion section 6A can obtain steady propulsive force working in the direction of the deep part of the large intestine, even if a part of the helical portion 51a is in contact with the folds of the sigmoid colon 503, or if the insertion section body 10 winds in an intricate manner. Further, the insertion section 6A has sufficient flexibility. Thus, the insertion section 6A smoothly advances along the intestinal wall without changing the lying shape of the sigmoid colon 503, which is easily changed in position.

Figure 10:
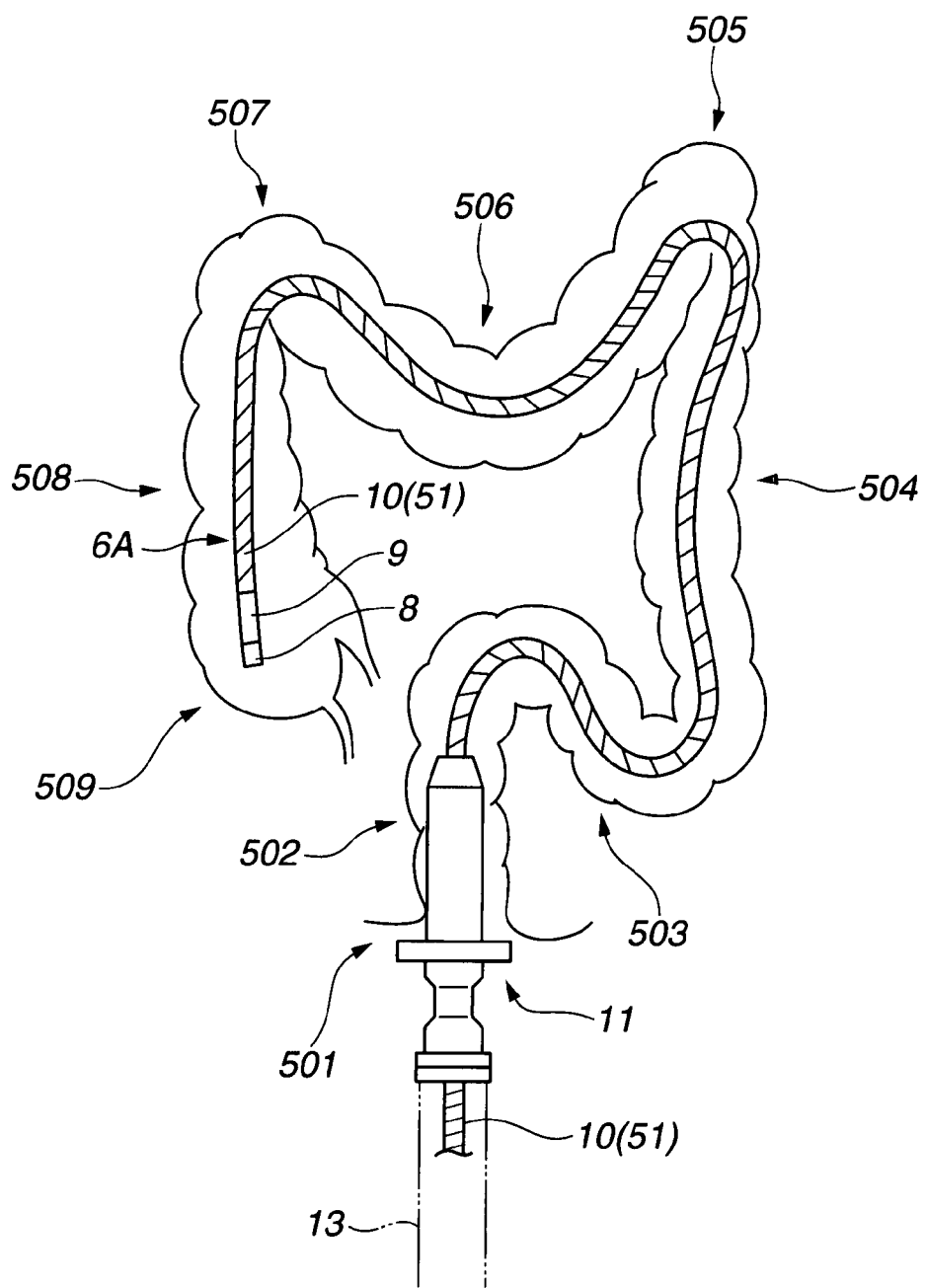
FIG. 10 is an explanatory diagram illustrating a state in which the insertion section body has reached the vicinity of the cecum.

After having passed the sigmoid colon 503, the insertion section 6A smoothly advances along the wall of the winding portion between the sigmoid colon 503 and the descending colon 504 of low mobility, the splenic flexure 505 between the descending colon 504 and the transverse colon 506 of high mobility, and the hepatic flexure 507 between the transverse colon 506 and the ascending colon 508. Then, as illustrated in FIG. 10, the insertion section 6A reaches the target site, such as the vicinity of the cecum 509, for example, without changing the lying shape of the large intestine.

In the insertion operation, when the distal end portion 8 has reached each of the winding portions, such as the splenic flexure 505 and the hepatic flexure 507, the surgeon operates the bending operation knobs 19 of the main operation section 18 while watching the endoscopic image displayed on the monitor 4, to thereby perform the operation of bending the bending portion 9 in accordance with the winding shape of the winding portion.

After having determined from the endoscopic image displayed on the monitor 4 that the distal end portion 8 has reached the vicinity of the cecum 509, the surgeon temporarily stops the rotation of the helical portion 51a through the foot or hand operation. Thereafter, through the foot operation of the foot switch 25 or the hand operation of the input device 72 of the main operation section 18, the surgeon performs an operation of rotating the helical portion 51a in the reverse direction to the direction of the axial rotation of the helical portion 51a performed in the insertion operation.

That is, the surgeon rotates the helical portion 51a in the reverse direction to the rotation direction of the insertion operation to perform an examination of the large intestine while moving the distal end portion 8 in the direction of withdrawing the distal end portion 8 from the vicinity of the cecum 509, i.e., while retreating the insertion section 6A. That is, even without a touch of a hand of the surgeon, the insertion section 6A is retreated by backward force applied to the helical portion 51a in the guide tube fixing member 64. Further, with the distal end portion 8 and the bending portion 9 pulled by the helical portion 51a due to the snap-fit function, the entirety of the insertion section 6A is retreated by the propulsive force of the helical portion 51a.

Upon confirmation of the arrival of the distal end portion 8 of the insertion section 6A at the insertion assisting device 11, the surgeon withdraws the insertion section 6A from the anus 501 of the patient together with the insertion assisting device 11, and completes the examination of the large intestine. In the above process, due to the backward force applied to the insertion section 6A in the guide tube fixing member 64, the insertion section 6A is stored in the insertion section storage case 12, bent in the original shape as illustrated in FIG. 7 described above.

As described above, according to the rotary self-propelled endoscope system 1 of the present embodiment, the surgeon can easily insert the insertion section 6A into the deep part of the body cavity, which is the large intestine in the present example, to perform endoscopy.

In the insertion operation of the insertion section body 10 into the body cavity, friction between the wall of the winding body cavity, such as the large intestine, and the rotating rotary tubular member 51 may be increased to interfere with the rotation of the rotary tubular member 51. In such a case, as described above, the rotary tubular member 51 applied with the torque by the motor 59 expands or contracts toward the outer or inner circumference thereof depending on the rotation direction, and expands and contracts in the longitudinal direction. In the present embodiment, the rotary tubular member 51 can expand and contract in the longitudinal direction due to the sliding movement of the proximal end-side ferrule 83. Thereby, the rotary tubular member 51 is prevented from becoming inflexible, and thus the deterioration of the insertability can be prevented.

However, under a frictional resistance exceeding a predetermined value, the rotary tubular member 51 is reduced in rotation speed, and the rotation of the rotary tubular member 51 is almost stopped.

In view of the above, to uninterruptedly perform the insertion operation of the insertion section 6A into the body cavity even under the above circumstance, the rotary self-propelled endoscope system 1 according to the present embodiment performs a torque control for changing, within a safe range, the limit value of the torque applied to the rotary tubular member 51. An example of such a torque control by the rotation control unit 66 of the control device 3 will be described with reference to FIGS. 11 and 12. In the rotary self-propelled endoscope system 1 according to the present embodiment, when the power is turned on to perform colonoscopy, the rotation control unit 66 of the control device 3 reads and executes a program illustrated in FIG. 11, which is stored in a not-illustrated memory. That is, the program illustrated in FIG. 11 is executed by the rotation control unit 66 during the use of the rotary self-propelled endoscope system 1.

Figure 11:
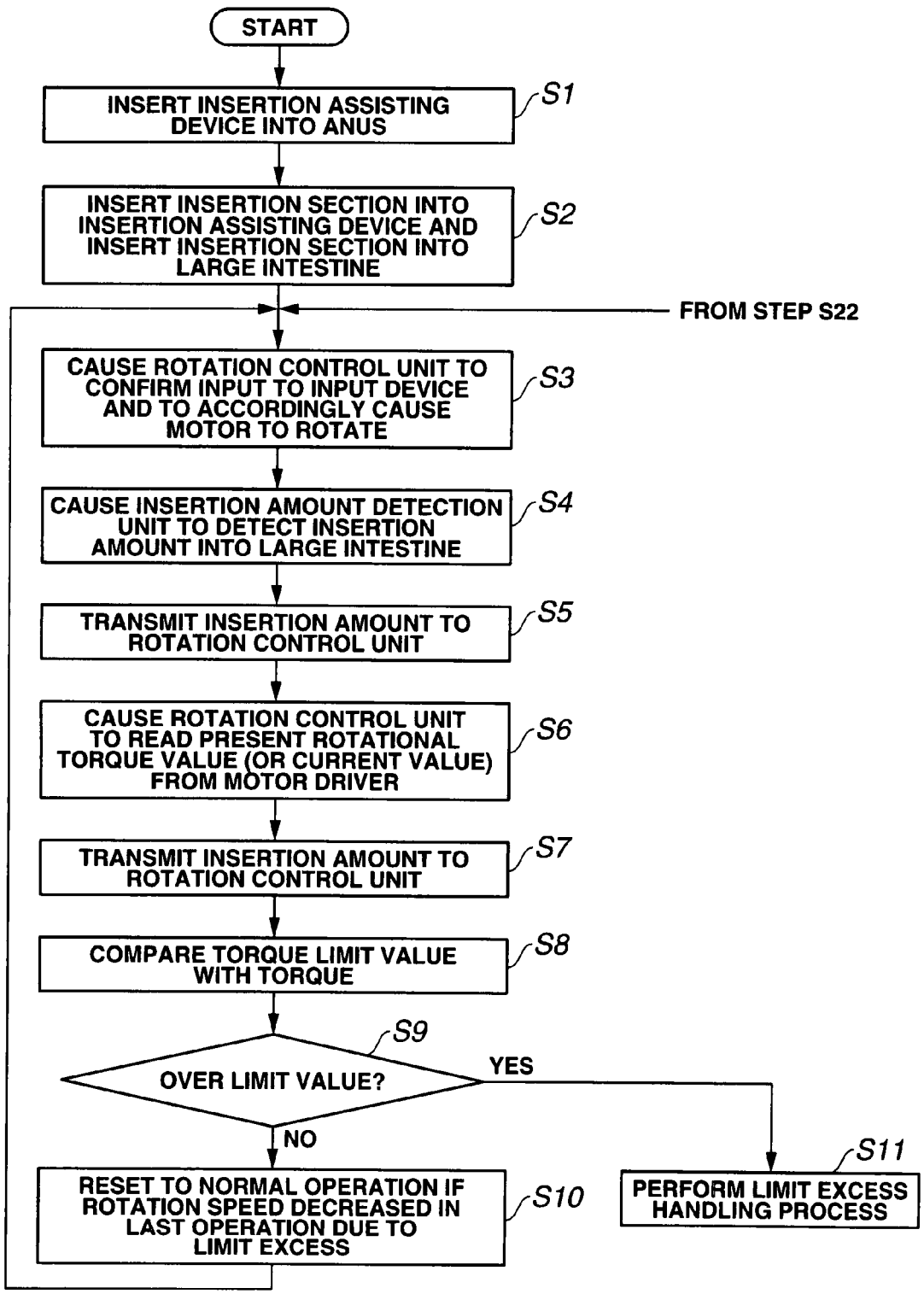
FIG. 11 is a flowchart for explaining the operation of the first embodiment, illustrating an example of the control performed by a rotation control unit of a control device.

As illustrated in FIG. 11, in the process of Step S1, the rotation control unit 66 confirms that the insertion assisting device 11 has been attached to the anus 501. Then, in the process of subsequent Step S2, the insertion section 6A is inserted into the insertion assisting device 11, as illustrated in FIGS. 8 and 9, and the rotation control unit 66 confirms the insertion of the insertion section 6A into the rectum 502 of the large intestine, as illustrated in FIG. 11.

In the process of subsequent Step S3, the rotation control unit 66 confirms the signal outputted on the basis of the foot operation of the foot switch 25 or the hand operation of the input device 72 of the main operation section 18 performed by the surgeon, and starts driving the motor 59 via the motor driver 67.

In the process of subsequent Step S4, the rotation control unit 66 detects, through the insertion amount detection unit 60, the insertion amount of the insertion section 6A into the large intestine. Then, in the process of subsequent Step S5, the result of the detection by the insertion amount detection unit 60 is transmitted to the rotation control unit 66.

Thereafter, in the process of subsequent Step S6, the rotation control unit 66 reads from the memory unit 71 the torque data value or the current value in accordance with the insertion amount, i.e., the result of the detection obtained from the insertion amount detection unit 60. Then, on the basis of the thus read torque data value or current value, the rotation control unit 66 sets the torque limit value 100, which is the limit value used in the drive control of the motor driver 67.

In the above process, in consideration of such factors as the individual variation among patients, the rotation control unit 66 can set torque limit values in accordance with the plurality of control phases, such as the torque limit values 100, 101, 102, and 103, for example, which are equal to or larger than the reference value of the torque limit value 100, as shown in FIG. 13.

In the process of subsequent Step S7, the rotation control unit 66 detects the present torque of the motor 59 from the motor driver 67, and retrieves the detected torque value. In the process, the rotation control unit 66 may alternatively retrieve the value of current supplied to the motor 59 by the motor driver 67.

In the process of subsequent Step S8, the rotation control unit 66 compares the retrieved torque value with the torque limit value shown in FIG. 13. In the comparison, if the present torque value is determined to be larger than the torque limit value in the determination process of Step S9, the rotation control unit 66 shifts the procedure to Step S11 to perform an anomaly determination process. Conversely, if the present torque value is determined to be equal to or smaller than the torque limit value, the rotation control unit 66 assumes that the rotary tubular member 51 is normally rotated and inserted, and shifts the procedure to Step S10.

In the process of the Step S10, if the rotation speed was reduced in the last operation due to the excess of the detected torque value over the torque limit value, the rotation control unit 66 resets the torque limit value to a specified value used in a normal state, i.e., the limit value which is a predetermined specified value, and returns the procedure to the Step S3.

Figure 12:
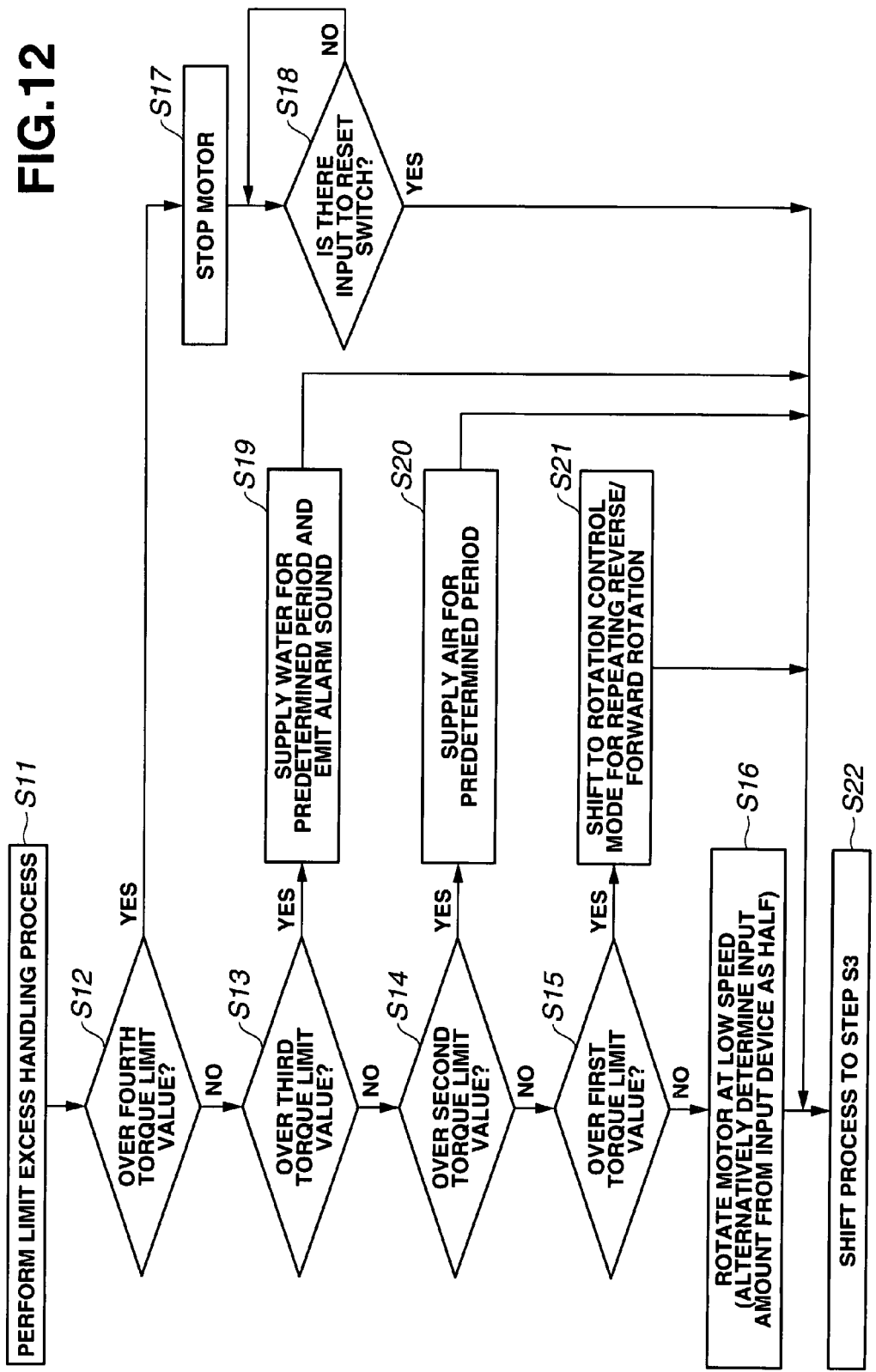
FIG. 12 is a flowchart illustrating a subroutine of the flowchart of FIG. 11, which is performed in a limit excess handling process.

When the procedure is shifted to the Step S11, the rotation control unit 66 reads from a not-illustrated storage unit the program of a limit excess handling routine illustrated in FIG. 12, and executes the program.

That is, as illustrated in FIG. 12, if the torque limit value is set in accordance with the plurality of control phases, for example, the rotation control unit 66 determines in the determination process of subsequent Step S12 whether or not the present torque value exceeds the fourth torque limit value 103, which is the largest torque limit value shown in FIG. 13. If the present torque value is determined not to exceed the fourth torque limit value 103, the rotation control unit 66 shifts the procedure to subsequent Step S13. Meanwhile, if the present torque value is determined to exceed the fourth torque limit value 103, the rotation control unit 66 shifts the procedure to Step S17.

The process of the Step S17 is performed when the present torque value is determined to exceed the fourth torque limit value 103. Therefore, the rotation control unit 66 determines the present state as a limit excess state, and stops supplying electric power to the motor 59 via the motor driver 67 in the process of the Step S17. That is, the rotation control unit 66 stops driving the motor 59. Thereafter, the rotation control unit 66 performs a control to simultaneously output an instruction signal for causing the buzzer 70 to issue an alarm and an instruction signal for causing the display unit 69 to activate an alarm light which acts as an alarm message. In the Step S17, the rotation control unit 66 may further cause the monitor 4 to display an alarm message via the image processing unit 68.

Thereafter, in the determination process of Step S118, the rotation control unit 66 determines whether or not a cancel operation has been performed. The determination in the Step S18 of whether or not the cancel operation has been performed is made on the basis of the operation of a not-illustrated reset switch provided to the control device 3, the foot switch 25, or the operation section 7, for example.

In the above, if the cancel operation is performed by the surgeon, the rotation control unit 66 returns the procedure to the above-described Step S3 illustrated in FIG. 11, as described in Step S22, to repeat the sequence of control operations. Meanwhile, if the cancel operation is not performed by the surgeon, the rotation control unit 66 repeats the determination process of the Step S18 until the cancel operation is performed.

In the process of the Step S13, determination is made on whether or not the present torque value exceeds the third torque limit value 102. If the present torque value is determined not to exceed the third torque limit value 102 in the Step S13, the rotation control unit 66 shifts the procedure to subsequent Step S14. Meanwhile, if the present torque value is determined to exceed the third torque limit value 102, the rotation control unit 66 shifts the procedure to Step S19.

The process of the Step S19 is performed when the present torque value is determined to exceed the third torque limit value 102. Therefore, to suppress the decrease in the rotational torque as much as possible, the rotation control unit 66 causes the sterilized water stored in the water supply tank 24 to be sent to the water supply tube 23b and ejected from the distal end portion 8 of the endoscope 2. In the process, the rotation control unit 66 outputs the instruction signal for causing the buzzer 70 to issue an alarm. Only the alarm sound from the buzzer 70 is emitted in the Step S19 to distinguish the above state from the state in which the present torque value exceeds the fourth torque limit value 103, i.e., the state in which the present torque value is over the largest limit value.

Then, in the process of the subsequent Step S22, the rotation control unit 66 returns the procedure to the above-described Step S3 illustrated in FIG. 11 to repeat the sequence of control operations.

In the process of the Step S14, determination is made on whether or not the present torque value exceeds the second torque limit value 101, which is smaller than the third torque limit value 102. If the present torque value is determined not to exceed the second torque limit value 101 in the Step S14, the rotation control unit 66 shifts the procedure to subsequent Step S115. Meanwhile, if the present torque value is determined to exceed the second torque limit value 101, the rotation control unit 66 shifts the procedure to Step S20.

The process of the Step S20 is performed when the present torque value is determined to exceed the second torque limit value 101. Therefore, to suppress the decrease in the rotational torque as much as possible, the rotation control unit 66 drives the not-illustrated compressor included in the control device 3 to cause the air sent from the compressor to be ejected from the distal end portion 8 of the endoscope 2 through the air supply tube 23a. Then, similarly as in the foregoing description, in the process of the subsequent Step S22, the rotation control unit 66 returns the procedure to the above-described Step S3 illustrated in FIG. 11 to repeat the sequence of control operations.

In the process of the Step S15, determination is made on whether or not the present torque value exceeds the first torque limit value 100, which is the smallest value serving as the reference value.

If the present torque value is determined not to exceed the first torque limit value 100 in the Step S15, the rotation control unit 66 shifts the procedure to subsequent Step S16. Meanwhile, if the present torque value is determined to exceed the first torque limit value 100, the rotation control unit 66 shifts the procedure to the process of Step S21.

The process of the Step S16 is performed when the present torque value is determined not to exceed the first torque limit value 100. Therefore, the rotation control unit 66 controls the motor driver 67 to rotate the motor 59 at a low speed. In the process, for example, the rotation control unit 66 may output a control signal to a not-illustrated rotation speed instruction unit of the input device 72 to control the motor 59 to perform low-speed rotation at a rotation speed half the normal speed on the basis of an instruction signal for reducing the rotation speed to one half of the normal speed. Then, similarly as in the foregoing description, in the process of the subsequent Step S22, the rotation control unit 66 returns the procedure to the above-described Step S3 illustrated in FIG. 11 to repeat the sequence of control operations.

Meanwhile, the process of the Step S21 is performed when the present torque value is determined to exceed the first torque limit value 100. Therefore, to suppress the decrease in the rotational torque as much as possible, the rotation control unit 66 controls the motor driver 67 to cause the motor 59 to repeat the reverse or forward rotation. Thereby, a rotation control mode for repeating the reverse or forward rotation of the motor 59 is activated. As a result, the insertion section 6A is advanced or retreated from the present position thereof in the body cavity, and the insertion of the insertion section 6A into the large intestine can be uninterruptedly continued. Thereafter, similarly as in the foregoing description, in the process of the subsequent Step S22, the rotation control unit 66 returns the procedure to the above-described Step S3 illustrated in FIG. 11 to repeat the sequence of control operations.

In the present embodiment, in setting the torque limit values 100, 101, 102, and 103 as shown in FIG. 13, for example, the rotation control unit 66 may set the torque limit values within a predetermined range or in an arbitrary manner in the insertion amounts LA1, LA2, LA3, and LA4.

In each of the insertion amounts LA1, LA2, LA3, and LA4, the torque limit value is set at a substantially constant value, as shown in FIG. 13, so that a space allowing the passage of the distal end portion 8 therethrough is formed in each of the winding portions corresponding to the insertion amounts LA1, LA2, LA3, and LA4.

Further, the respective torque limit values 100, 101, 102, and 103 shown in FIG. 13 are rapidly increased in the transition periods to the insertion amounts LA1, LA2, LA3, and LA4. The rapid increase of the torque limit values is caused by a rapid increase of the frictional resistance in the winding portions corresponding to the insertion amounts LA1, LA2, LA3, and LA4, which is caused by the contact of the distal end portion 8 and the rotary tubular member 51 with the wall of the body cavity.

According to the above-described control flow executed by the rotation control unit 66 of the control device 3, therefore, the rotary self-propelled endoscope system 1 of the present embodiment can perform the torque control of changing, within a safe range, the limit value of the torque applied to the rotary tubular member 51. Accordingly, the insertion of the insertion section 6A into the body cavity can be uninterruptedly performed without a stop of the rotational movement of the rotary tubular member 51. As a result, the insertability of the insertion section 6A into the body cavity is improved.

In the first embodiment, description has been mainly made of the torque control performed in the insertion of the insertion section 6A of the rotary self-propelled endoscope 2 into the large intestine. Needless to say, the torque control can also be applied to the withdrawal of the insertion section 6A from inside the body cavity, such as the large intestine.

Figure 14:
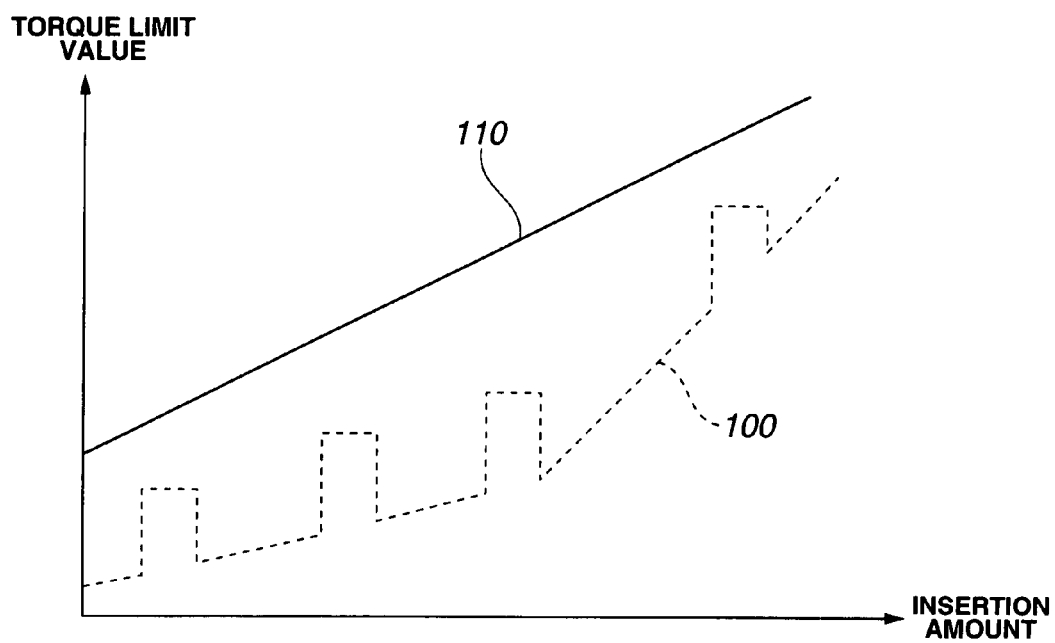
FIG. 14 is a graph showing a torque limit value in accordance with the insertion amount, which is used in torque control performed by the rotation control unit in the withdrawal of the insertion section.

For the withdrawal of the insertion section 6A from inside the body cavity, such as the large intestine, the rotation control unit 66 sets a withdrawal torque limit value 110 as shown in FIG. 14, for example. The withdrawal torque limit value 110 is larger than, for example, the first torque limit value 100, which is one of the torque limit values set in the above-described first embodiment. Further, the withdrawal torque limit value 110 has a substantially proportional relationship to the insertion amount. In withdrawing the insertion section 6A from inside the body cavity, the rotation control unit 66 can control the motor driver 67 to rotate the motor 59 in the reverse direction on the basis of the withdrawal torque limit value 110.

That is, in the withdrawal of the insertion section 6A from the large intestine, a particularly large frictional resistance does not act on the rotary tubular member 51. Thus, the insertion section 6A can be smoothly withdrawn in a normal situation. To prepare for the occurrence of a frictional resistance greater than expected, however, the withdrawal torque limit value 110 is set to be larger than the torque limit value set for the insertion operation. Accordingly, the withdrawal movement of the insertion section 6A can be uninterruptedly performed in the withdrawal of the insertion section 6A from inside the body cavity, such as the large intestine. As a result, the usability is improved.

Figure 15:
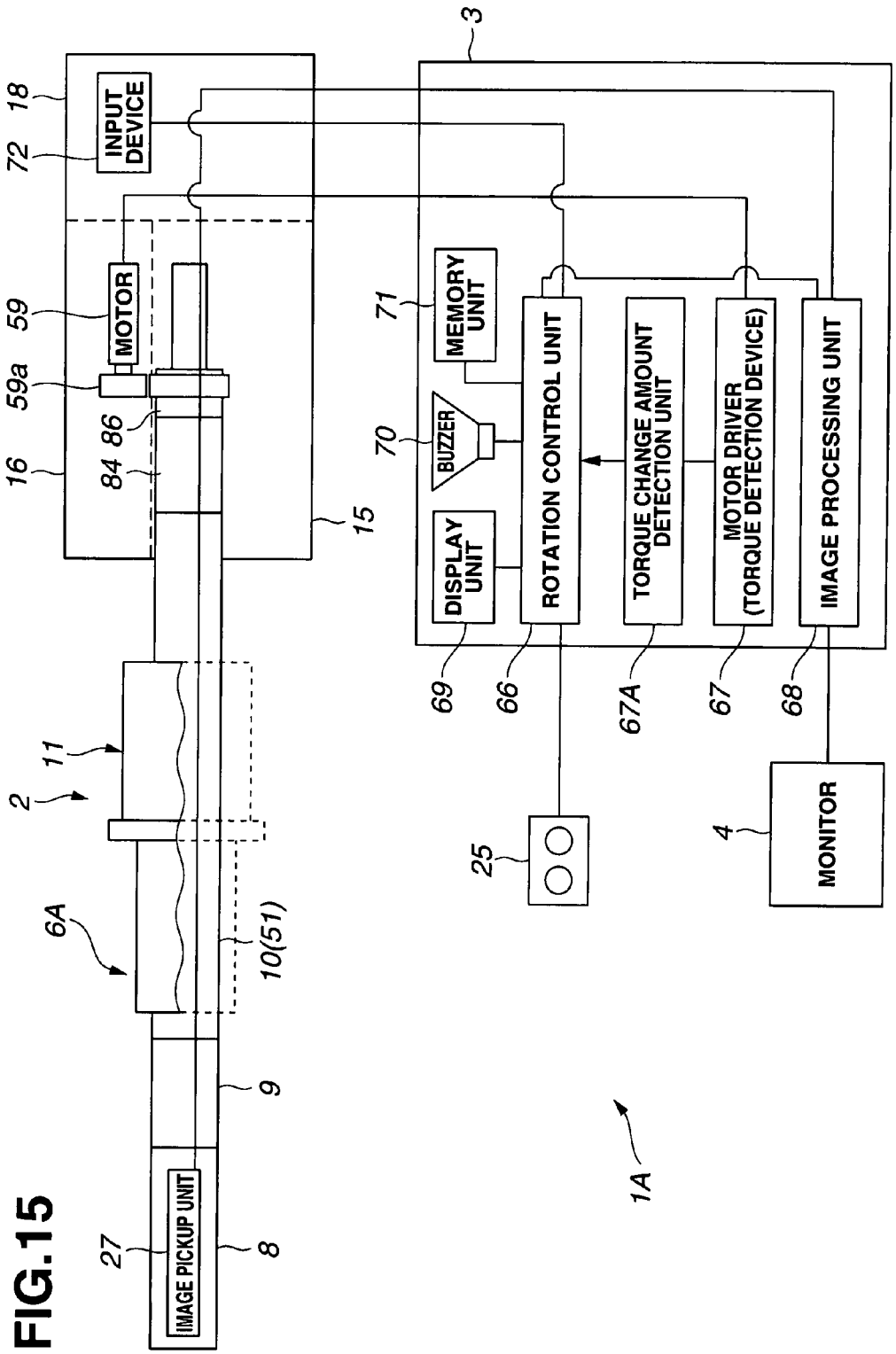
FIG. 15 is a block diagram illustrating an overall electrical configuration of a rotary self-propelled endoscope system according to a second embodiment of the present invention.
Figure 16:
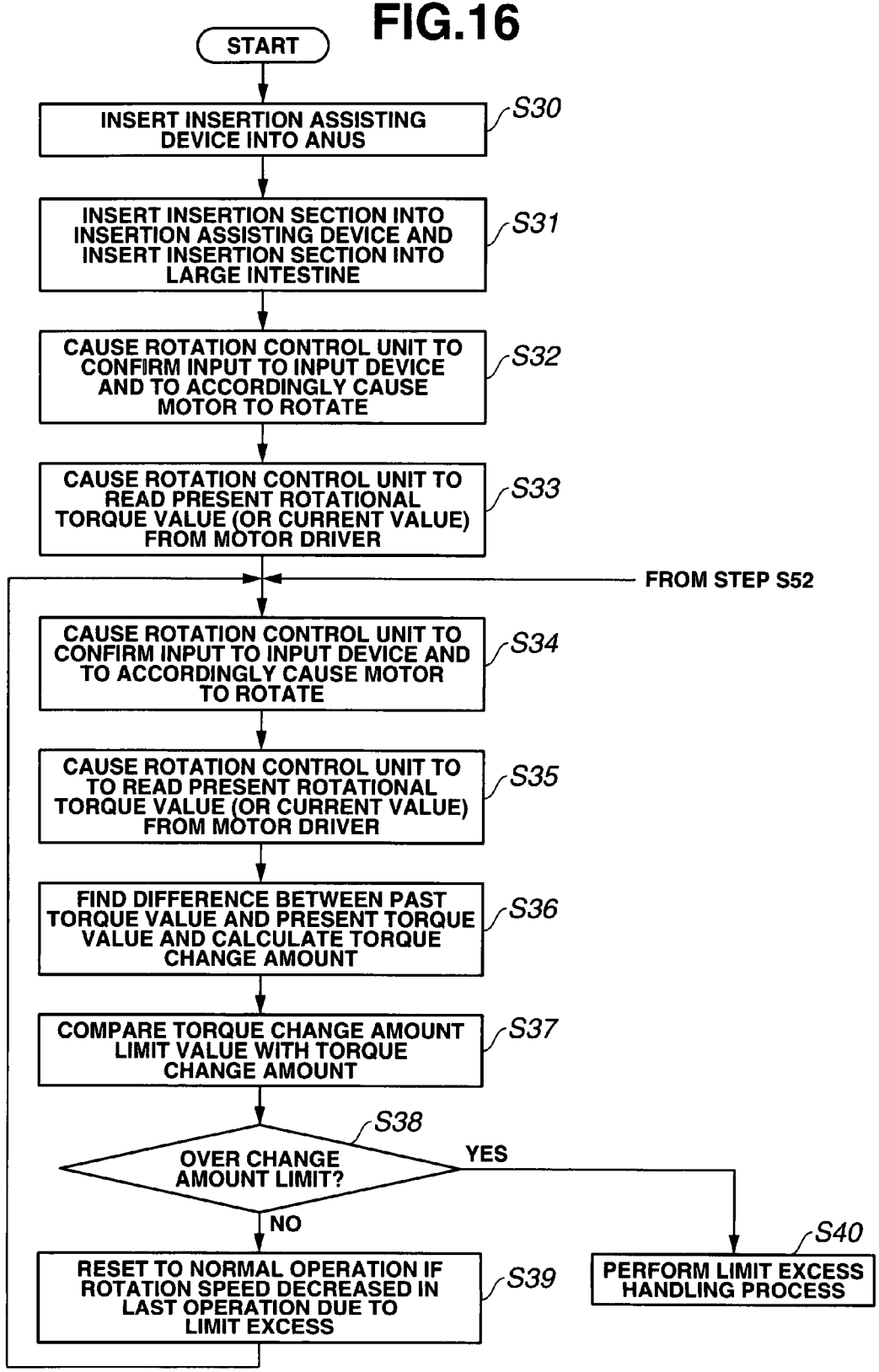
FIG. 16 is a flowchart for explaining the operation of the second embodiment, illustrating an example of the control performed by the rotation control unit of the control device.
Figure 17:
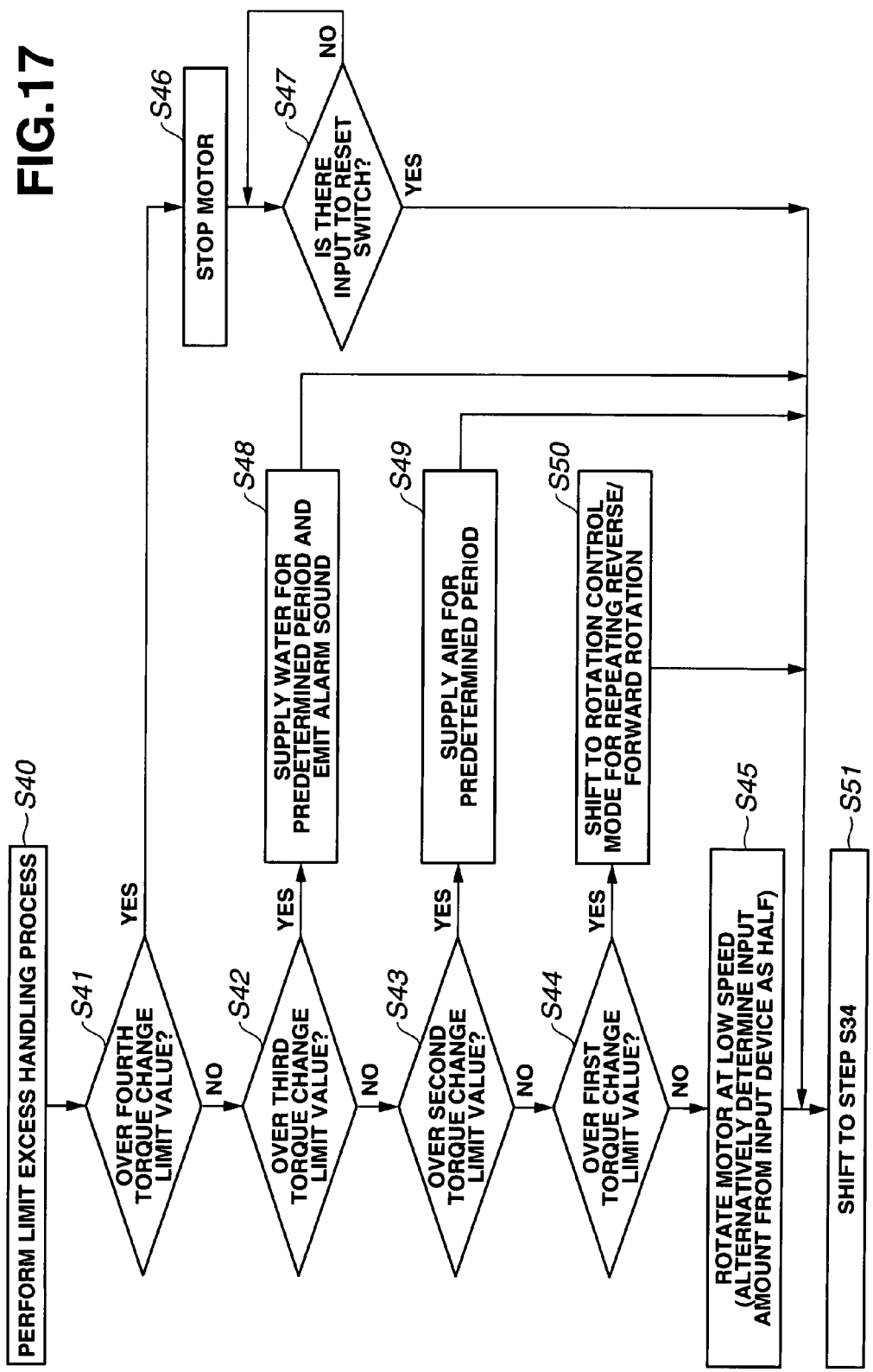
FIG. 17 is a flowchart illustrating a subroutine of the flowchart of FIG. 16, which is performed in a limit excess handling process.

With reference to FIG. 15 to 17, a rotary self-propelled endoscope system 1A according to a second embodiment will now be described. In FIG. 15 to 17, similar components to the components of the first embodiment will be assigned with the same reference numerals, and description thereof will be omitted. Only different components from the components of the first embodiment will be described.

In the present embodiment, the torque is detected by the motor driver 67, which serves as the torque detection unit, and the amount of change in the detected torque is calculated. Then, the calculated change amount of the torque is associated with the preset insertion amount of the insertion section 6A, and is set as a torque change limit value in accordance with the insertion amount.

Specifically, as illustrated in FIG. 15, the rotary self-propelled endoscope system 1A according to the second embodiment is substantially similar in configuration to the rotary self-propelled endoscope system 1 according to the first embodiment. However, the rotary self-propelled endoscope system 1A is provided with a torque change amount detection unit 67A in the control device 3, in place of the insertion amount detection unit 60 provided in the insertion assisting device 11.

The torque change amount detection unit 67A is electrically connected between the motor driver 67 and the rotation control unit 66. The torque change amount detection unit 67A calculates the change amount of the torque of the motor 59 detected by the motor driver 67, and outputs the calculated torque change amount to the rotation control unit 66. In the above description, the torque change amount detection unit 67A calculates the torque change amount from the inputted torque. Alternatively, the torque change amount detection unit 67A may retrieve the value of current supplied to the motor 59 by the motor driver 67, calculate the change amount of the current value, and output the calculated change amount of the current value to the rotation control unit 66. Then, as shown in FIG. 18, on the basis of the inputted torque change amount, which is associated with the preset insertion amount of the insertion section 6A, the rotation control unit 66 sets a torque change limit value 100A in accordance with the insertion amount.

Figure 18:
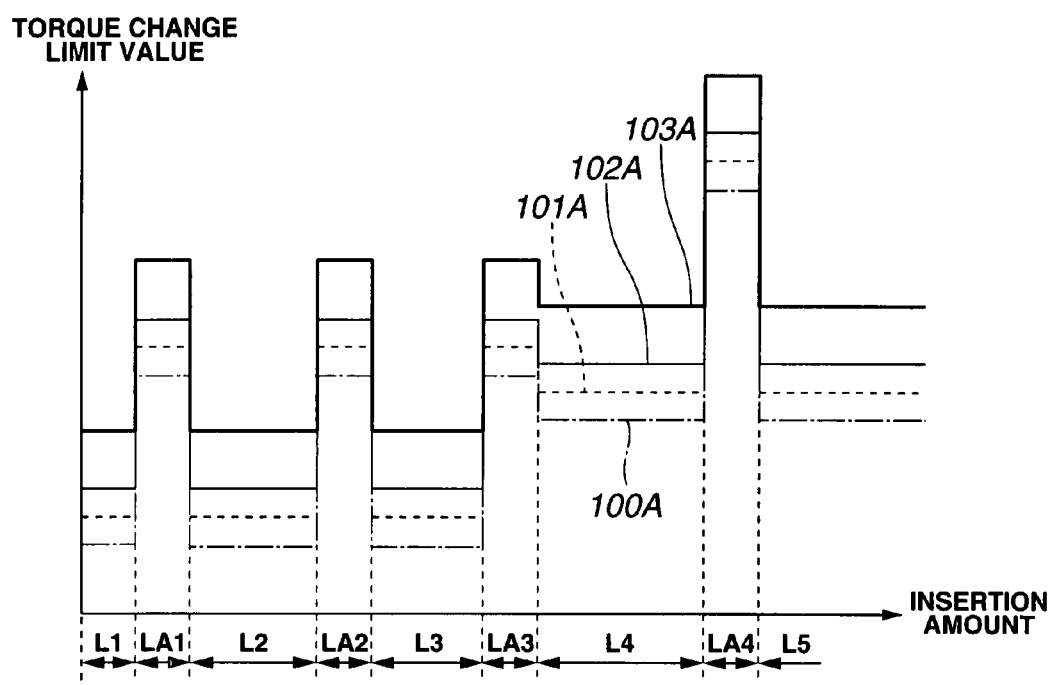
FIG. 18 is a graph showing torque change limit values in accordance with insertion amounts, which are used in determination control performed by the rotation control unit.

Also in the present embodiment, similarly as in the first embodiment, in consideration of the individual variation among patients, and using the torque change limit value 100A as the reference value, the rotation control unit 66 can set torque change limit values equal to or larger than the value in accordance with a plurality of control phases, such as the torque change limit values 100A, 101A, 102A, and 103A, for example, as shown in FIG. 18.

In the present embodiment, the first torque change limit value 100A serving as the reference value and indicated by the alternate long and short dash line in FIG. 18 is set through the control by the rotation control unit 66.

If the torque change limit values in accordance with the plurality of control phase are unnecessary, only the first torque change limit value 100A serving as the reference value may be set. Further, to switch between the setting of only the first torque change limit value 100A and the setting of the first torque change limit value 100A to the fourth torque change limit value 103A, for example, in accordance with the plurality of control phases, the mode selecting operation is performed through the input device 72 to switch the setting, similarly as in the first embodiment.

To activate a mode for switching the torque change limit value in accordance with the plurality of control phases from the first torque change limit value 100A to the fourth torque change limit value 103A, for example, the respective torque change limit values 100A, 101A, 102A, and 103A are set, as shown in FIG. 18. That is, as indicated by the broken line in the figure, the second torque change limit value 101A is larger than the first torque change limit value 100A. Further, as indicated by the thin solid line in the figure, the third torque change limit value 102A is larger than the second torque change limit value 101A. Furthermore, as indicated by the thick solid line in the figure, the fourth torque change limit value 103A is larger than the third torque change limit value 102A. The torque change limit values are not limited to the above torque change limit values 100A, 101A, 102a, and 103A. Thus, a further plurality of torque change limit values may be set in addition to the above torque change limit values.

The insertion amounts shown in FIG. 18 are preset and previously stored in the memory unit 71, for example. The data of the insertion amounts is read by the rotation control unit 66 in setting the torque change limit value. The respective ranges of the insertion amounts shown in FIG. 18 correspond to the respective sites in the large intestine, similarly as in the first embodiment. Further, the respective ranges can be arbitrarily changed and set. In other aspects of the configuration, the present embodiment is similar to the first embodiment.

With reference to FIGS. 16 and 17, the operation of the rotary self-propelled endoscope system 1A according to the second embodiment will now be described. The second embodiment is similar to the first embodiment in the basic operation of the rotary self-propelled endoscope 2, and thus description thereof will be omitted.

In the rotary self-propelled endoscope system 1A of the present embodiment, when the power is turned on to perform colonoscopy, the rotation control unit 66 of the control device 3 reads and executes a program illustrated in FIG. 16, which is stored in the not-illustrated memory included in the rotation control unit 66. That is, the program illustrated in FIG. 16 is executed by the rotation control unit 66 during the use of the rotary self-propelled endoscope system 1A.

As illustrated in FIG. 16, in the process of Step S30, the rotation control unit 66 confirms that the insertion assisting device 11 has been attached to the anus 501. Then, in the process of subsequent Step S31, the insertion section 6A is inserted into the insertion assisting device 11, as illustrated in FIGS. 8 and 9, and the rotation control unit 66 confirms the insertion of the insertion section 6A into the rectum 502 of the large intestine, as illustrated in FIG. 16.

In the process of subsequent Step S32, the rotation control unit 66 confirms the signal outputted on the basis of the foot operation of the foot switch 25 or the hand operation of the input device 72 of the main operation section 18 performed by the surgeon, and starts driving the motor 59 via the motor driver 67.

In the process of subsequent Step S33, the rotation control unit 66 causes the motor driver 67 to detect the present torque value of the motor 59, and retrieves the result of the detection. To calculate the change amount of the torque value, the retrieved torque value is temporarily stored in a not-illustrated storage unit included in the rotation control unit 66.

Thereafter, in the process of subsequent Step S34, the rotation control unit 66 continues to confirm the signal outputted on the basis of the operation of the foot switch 25 or the input device 72 performed by the surgeon, and drives the motor 59 via the motor driver 67 to rotate the rotary tubular member 51.

In the process of subsequent Step S35, the rotation control unit 66 detects the present torque value of the motor 59 from the motor driver 67. Then, in the process of subsequent Step S36, the rotation control unit 66 calculates, through the torque change amount detection unit 67A, the torque change amount, which is the difference between the past torque value stored in the not-illustrated storage unit and the presently retrieved torque value.

Then, on the basis of the calculated torque change amount, which is associated with the preset insertion amount read from the memory unit 71, the rotation control unit 66 sets the torque change limit value 100A used in the drive control of the motor driver 67.

In the above process, similarly as in the first embodiment, in consideration of the individual variation among patients, and in accordance with the input operation on the input device 72, the rotation control unit 66 may set the torque change limit values in accordance with the plurality of control phases equal to or larger than the reference value of the torque change limit value 100A, such as the torque change limit values 100A, 101A, 102A, and 103A, for example, as shown in FIG. 18.

In the process of subsequent Step S37, the rotation control unit 66 compares the torque change amount calculated by the torque change amount detection unit 67A with the torque change limit value shown in FIG. 18. In the comparison, if the torque change amount is determined to be larger than the torque change limit value in the determination process of Step S38, the rotation control unit 66 shifts the procedure to Step S40 to perform a limit excess handling process. Meanwhile, if the torque change amount is determined to be equal to or smaller than the torque change limit value in the Step S38, the rotation control unit 66 assumes that the rotary tubular member 51 is normally rotated and inserted, and shifts the procedure to Step S39.

In the process of the Step S39, if the rotation speed was reduced in the last operation due to the excess of the obtained torque change amount over the torque change limit value, the rotation control unit 66 resets the torque change limit value to a predetermined specified value, i.e., a specified value used in a normal state, and returns the procedure to the above-described Step S34.

Meanwhile, if the procedure is shifted to the Step S40, the rotation control unit 66 reads from the not-illustrated storage unit the program of a limit excess handling routine illustrated in FIG. 17, and executes the program.

That is, as illustrated in FIG. 17, substantially similarly as in the program of the first embodiment illustrated in FIG. 12, if the torque change limit value is set in accordance with the plurality of control phases, for example, the rotation control unit 66 determines in the determination process of subsequent Step S41 whether or not the present torque change amount exceeds the fourth torque change limit value 103A, which is the largest torque change limit value shown in FIG. 18. In the determination, if the present torque change amount is determined not to exceed the fourth torque change limit value 103A, the rotation control unit 66 shifts the procedure to subsequent Step S42. Meanwhile, if the present torque change amount is determined to exceed the fourth torque change limit value 103A, the rotation control unit 66 shifts the procedure to Step S46.

The process of the Step S46 is performed when the present torque change amount is determined to exceed the fourth torque change limit value 103A. Therefore, the rotation control unit 66 determines the present state as a limit excess state, and stops supplying electric power to the motor 59 via the motor driver 67. That is, the rotation control unit 66 stops driving the motor 59. Thereafter, the rotation control unit 66 performs a control to simultaneously output an instruction signal for causing the buzzer 70 to issue an alarm and an instruction signal for causing the display unit 69 to activate an alarm light acting as an alarm message. In the Step S46, the rotation control unit 66 may further cause the monitor 4 to display an alarm message via the image processing unit 68.

Thereafter, in the determination process of Step S47, the rotation control unit 66 determines whether or not a cancel operation has been performed. The determination in the Step S47 of whether or not the cancel operation has been performed is made on the basis of the operation of a not-illustrated reset switch provided to the control device 3, the foot switch 25, or the operation section 7, for example.

In the above, if the cancel operation is performed by the surgeon, the rotation control unit 66 returns the procedure to the above-described Step S34 illustrated in FIG. 16, as described in Step S51, to repeat the sequence of control operations. Meanwhile, if the cancel operation is not performed by the surgeon, the rotation control unit 66 repeats the determination process of the Step S47 until the cancel operation is performed.

In the process of the Step S42, determination is made on whether or not the torque change amount exceeds the third torque change limit value 102A. If the torque change amount is determined not to exceed the third torque change limit value 102A in the Step S42, the rotation control unit 66 shifts the procedure to subsequent Step S43. Meanwhile, if the torque change amount is determined to exceed the third torque change limit value 102A, the rotation control unit 66 shifts the procedure to Step S48.

The process of the Step S48 is performed when the torque change amount is determined to exceed the third torque change limit value 102A. Therefore, to suppress the decrease in the rotational torque as much as possible, the rotation control unit 66 causes the sterilized water stored in the water supply tank 24 to be sent to the water supply tube 23b and ejected from the distal end portion 8 of the endoscope 2. In the process, the rotation control unit 66 outputs the instruction signal for causing the buzzer 70 to issue an alarm. Only the alarm sound from the buzzer 70 is emitted in the Step S48 to distinguish the above state from the state in which the torque change amount exceeds the fourth torque change limit value 103A.

Then, in the process of the subsequent Step S51, the rotation control unit 66 returns the procedure to the above-described Step S34 illustrated in FIG. 16 to repeat the sequence of control operations.

In the process of the Step S43, determination is made on whether or not the torque change amount exceeds the second torque change limit value 101A (see FIG. 18), which is smaller than the third torque change limit value 102A. If the torque change amount is determined not to exceed the second torque change limit value 101A in the Step S43, the rotation control unit 66 shifts the procedure to subsequent Step S44. Meanwhile, if the torque change amount is determined to exceed the second torque change limit value 101A, the rotation control unit 66 shifts the procedure to the process of Step S49.

The process of the Step S49 is performed when the torque change amount is determined to exceed the second torque change limit value 101A. Therefore, to suppress the decrease in the rotational torque as much as possible, the rotation control unit 66 drives the not-illustrated compressor included in the control device 3 to cause the air sent from the compressor to be ejected from the distal end portion 8 of the endoscope 2 through the air supply tube 23*a*. Then, similarly as in the foregoing description, in the process of the subsequent Step S51, the rotation control unit 66 returns the procedure to the above-described Step S34 illustrated in FIG. 16 to repeat the sequence of control operations.

In the process of the Step S44, determination is made on whether or not the torque change amount exceeds the first torque change limit value 100A (see FIG. 18), which is the smallest value serving as the reference value.

If the torque change amount is determined not to exceed the first torque change limit value 100A in the Step S44, the rotation control unit 66 shifts the procedure to subsequent Step S45. Meanwhile, if the torque change amount is determined to exceed the first torque change limit value 100A, the rotation control unit 66 shifts the procedure to the process of Step S50.

The process of the Step S45 is performed when the torque change amount is determined not to exceed the first torque change limit value 100A. Therefore, the rotation control unit 66 controls the motor driver 67 to rotate the motor 59 at a low speed. In the process, for example, the rotation control unit 66 may output a control signal to the not-illustrated rotation speed instruction unit of the input device 72 to control the motor 59 to perform low-speed rotation at a rotation speed half the normal speed on the basis of an actuating signal for reducing the rotation speed to one half of the normal speed. Then, similarly as in the foregoing description, in the process of the subsequent Step S51, the rotation control unit 66 returns the procedure to the above-described Step S34 illustrated in FIG. 16 to repeat the sequence of control operations.

Meanwhile, the process of the Step S50 is performed when the torque change amount is determined to exceed the first torque change limit value 100A. Therefore, to suppress the decrease in the rotational torque as much as possible, the rotation control unit 66 controls the motor driver 67 to cause the motor 59 to repeat the reverse or forward rotation. Thereby, the rotation control mode for repeating the reverse or forward rotation of the motor 59 is activated. As a result, the insertion section 6A is advanced or retreated from the present position thereof in the body cavity, and the insertion of the insertion section 6A into the large intestine can be uninterruptedly continued. Thereafter, similarly as in the foregoing description, in the process of the subsequent Step S51, the rotation control unit 66 returns the procedure to the above-described Step S34 illustrated in FIG. 16 to repeat the sequence of control operations. According to the second embodiment, therefore, substantially similar effect as the effects of the foregoing first embodiment can be obtained with no need to provide the insertion amount detection unit 60 employed in the first embodiment.

In the above description, as described in the Step S20 of the first embodiment in FIG. 12 and the Step S49 of the second embodiment in FIG. 17, the air supply operation is performed for a predetermined time period if the present torque value exceeds the second torque limit value 101, or if the torque change amount exceeds the second torque change limit value 101A, for example. However, the method of controlling the air supply is not limited to the above.

Figure 19:
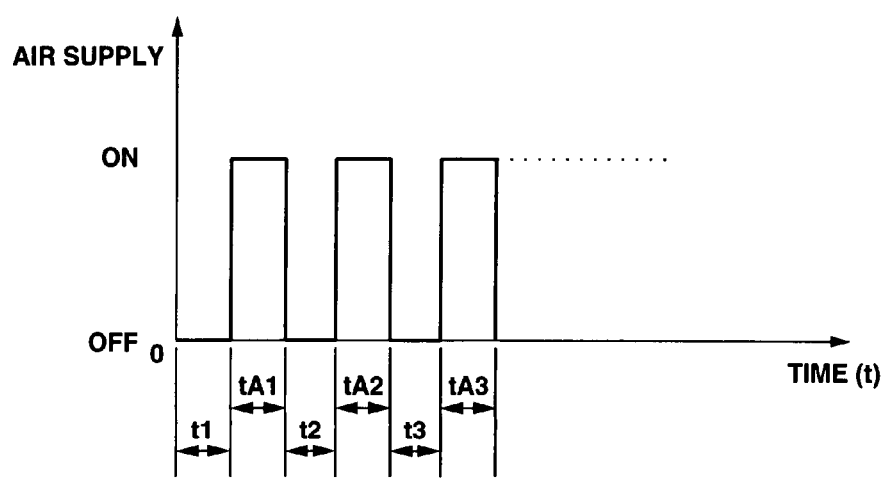
FIG. 19 is a timing diagram used in air or water supply control performed by the rotation control unit.

For example, when the procedure is shifted to the Step S20 of FIG. 12 or the Step S49 of FIG. 17, the rotation control unit 66 may perform a control to turn on and off the driving of the air supply operation at predetermined intervals, as shown in FIG. 19. Further, irrespective of the process of the Step S20 or the Step S49, the rotation control unit 66 may perform a control to turn on the driving of the air supply operation only in the winding portions corresponding to the insertion amounts LA1, LA2, and LA3 between the insertion amounts L1, L2, L3, and L4 of the insertion section 6A, in which the insertion operation is difficult to perform.

In the above case, a predetermined amount of air is supplied at predetermined intervals, with an air supply stop time t and an air supply time tA respectively set as t1=t2=t3=t4 and tA1=tA2=tA3, for example. Alternatively, the air supply may be performed in accordance with the insertion speed, with the air supply stop time t and the air supply time tA respectively set as t1>t2>t3>t4 and tA1=tA2=tA3, for example.

The drive timings as shown in FIG. 19 are not limited to the air supply operation, and thus may be employed in driving the water supply operation performed in, for example, the Step S19 of the first embodiment and the Step S48 of the second embodiment.

Figure 20:
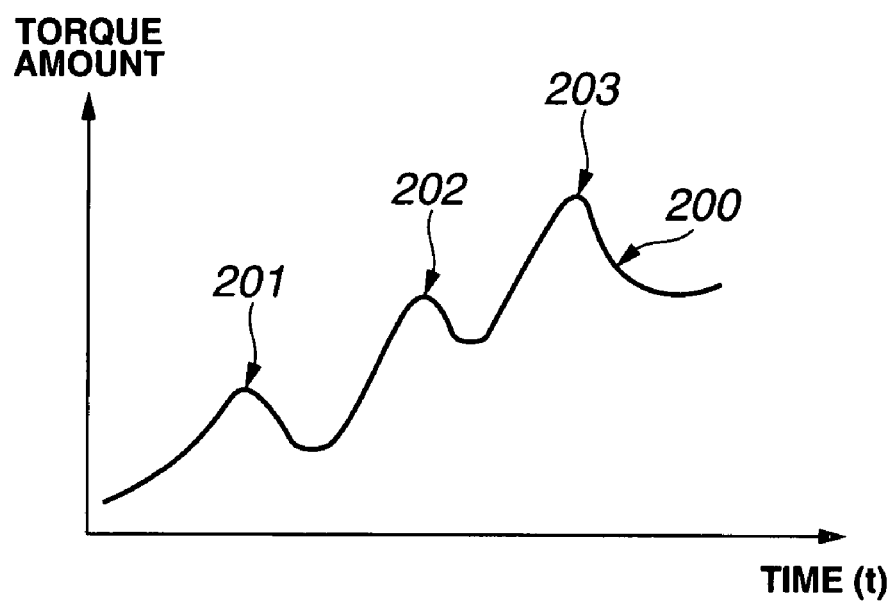
FIG. 20 is a characteristic diagram for explaining another air or water supply control method performed by the rotation control unit.

Further, in the air or water supply operation in the first and second embodiments, as illustrated in FIG. 20, the rotation control unit 66 may perform a control to perform the air or water supply operation on the basis of an air or water supply amount characteristic 200, which is based on the detected torque amount or the torque change amount and the time t.

In the above case, air or water supply amounts 201, 202, and 203 correspond to the respective ranges of the insertion amounts LA1, LA2, and LA3 illustrated in FIG. 13, which correspond to the respective winding portions. That is, the air or water supply amount is increased as the insertion section 6A is inserted toward the deep winding portions, in which the insertion of the insertion section 6A is difficult to perform. Accordingly, the frictional resistance of the rotary tubular member 51 is reduced, and the insertion section 6A can be smoothly inserted into the deep part.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A rotary self-propelled endoscope system comprising:
    a flexible insertion section body which includes, in a distal end portion thereof, a rigid distal end portion including an image pickup apparatus, and which is inserted into a body cavity;
    an insertion section rotatably fit to the outside of the insertion section body and including a rotary tubular member having a helical portion formed by a helical concave-convex portion;
    a drive unit for applying the rotary tubular member with axial and rotational drive force;
    a torque detection unit for detecting torque information of the rotary tubular member;
    a memory unit in which a limit value for controlling a preset torque of the rotary tubular member is changeably stored; and
    a control unit for comparing, on the basis of the torque information detected by the torque detection unit, a present value with the limit value obtained from the memory unit, and controlling the drive unit on the basis of the result of the comparison, the control unit changing and setting the limit value of the change amount in accordance with the change amount of the torque, and compares the set limit value with the change amount of the torque, wherein:

the torque information being a change amount of the torque which is a difference between a torque value stored in the memory unit and a presently retrieved torque value detected by the torque detection unit.

2. The rotary self-propelled endoscope system according to claim 1, wherein, if present torque information detected by the torque detection unit is larger than a limit value in a last operation, or if the change amount of the torque detected by the torque detection unit is larger than a torque change limit value in the last operation, the control unit controls the drive unit to stop the rotation of the rotary tubular member or to reduce the torque of the rotary tubular member, and if the present torque information is smaller than the
limit value in the last operation, or if the change amount of the torque is smaller than the torque change limit value in the last operation, the control unit determines that the rotary tubular
member is normally rotating, and then, if a rotation speed is reduced over the limit value in the last operation or the torque change limit value in the last operation, the rotation control unit resets the limit value or torque change limit value to a specified value used in a normal state.

3. The rotary self-propelled endoscope system according to claim 2, wherein the limit value of the change amount is set in a plurality of patterns of different limit torque values or torque change limit values in accordance with a plurality of control phases including a state inside the body cavity and an insertion site.

4. The rotary self-propelled endoscope system according to claim 1, wherein a withdrawal limit value of a change amount of the torque used in withdrawing the insertion section inserted into the body cavity is set to be larger than an insertion limit value of the change amount of the torque used in inserting the insertion section into the body cavity.

5. The rotary self-propelled endoscope system according to claim 1, further comprising a storage unit, wherein a torque data value which is controllable by the control unit in data writing and data reading is stored in the storage unit.

6. The rotary self-propelled endoscope system according to claim 1, wherein the control unit controls the drive unit to rotate the rotary tubular member to rotate at a predetermined rotation speed.

* * * * *